US012605277B2

(12) United States Patent
Blazevich

(10) Patent No.: US 12,605,277 B2
(45) Date of Patent: Apr. 21, 2026

(54) EYE DROP DISPENSER

(71) Applicant: John Z. Blazevich, Palos Verdes Peninsula, CA (US)

(72) Inventor: John Z. Blazevich, Palos Verdes Peninsula, CA (US)

( * ) Notice: Subject to any disclaimer, the term of this patent is extended or adjusted under 35 U.S.C. 154(b) by 0 days.

(21) Appl. No.: 19/309,405

(22) Filed: Aug. 25, 2025

(65) Prior Publication Data

US 2026/0053666 A1 Feb. 26, 2026

Related U.S. Application Data

(63) Continuation of application No. 18/907,367, filed on Oct. 4, 2024, now Pat. No. 12,403,035, which is a
(Continued)

(51) Int. Cl.
*A61F 9/00* (2006.01)
*A61M 35/00* (2006.01)
*B65D 47/18* (2006.01)

(52) U.S. Cl.
CPC ......... *A61F 9/0026* (2013.01); *A61M 35/003* (2013.01); *B65D 47/18* (2013.01)

(58) Field of Classification Search
CPC ... A61F 9/0026; A61F 9/0008; A61M 35/003; A61M 11/00; A61M 11/008; B65D 47/18; B65D 35/28; B65D 83/0055; B65D 35/14; A61H 35/02; A61J 1/067; B05B 11/0013; B05B 11/00446; B05B 11/0037; B05B 11/0054
See application file for complete search history.

(56) References Cited

U.S. PATENT DOCUMENTS 2,209,192 A 7/1940 Demsey
2,231,112 A 2/1941 Conner
(Continued)

FOREIGN PATENT DOCUMENTS

AU 1388392 A 2/1993
CA 132553 S 5/2010
(Continued)

OTHER PUBLICATIONS

Anonymous: "Lansier—Del 23 al 25 de Agosto, 2018 se llevó a cabo el XXVII Congreso Peruano de Oftalmología en el Hotel Westin", Oct. 11, 2018, Retrieved from the Internet: URL: https://www.facebook.com/lansieroeru/posts/683669075353022/.
(Continued)

*Primary Examiner* — Rebecca E Eisenberg
*Assistant Examiner* — Brandon W. Levy
(74) *Attorney, Agent, or Firm* — Knobbe, Martens, Olson & Bear, LLP

(57) ABSTRACT

A dispenser assembly includes a dispenser bottle having a nipple for dispensing a solution (e.g., eye drop solution, eye wash solution, eye lid cleaner and/or wash solution), and a cap removably couplable to the dispenser bottle over the nipple. The dispenser bottle has a chamber that removably receives a single-use vial cartridge. An eye cup is fixedly coupled to the dispenser bottle around the nipple, or the eye cup is detachable and invertible relative to the dispenser bottle. The eye cup can be supported on or rest on the periphery of the eye socket to facilitate delivery of the solution onto or over a user's eye.

20 Claims, 33 Drawing Sheets

Related U.S. Application Data continuation-in-part of application No. 18/654,342, filed on May 3, 2024, now Pat. No. 12,127,978.

(56) References Cited

U.S. PATENT DOCUMENTS

| | | | |
|---|---|---|---|
| 2,516,818 A | | 7/1950 | West |
| 2,826,194 A | | 3/1958 | Seymour |
| 3,058,466 A | | 10/1962 | Routsong |
| 3,223,289 A | * | 12/1965 | Bouet .................. B65D 83/771 |
| | | | 401/153 |
| 3,872,865 A | | 3/1975 | Casey |
| 3,945,381 A | | 3/1976 | Silver |
| 4,002,168 A | | 1/1977 | Petterson |
| 4,085,750 A | * | 4/1978 | Bosshold .............. A61F 9/0026 |
| | | | 604/302 |
| 4,468,103 A | | 8/1984 | Meckler |
| 4,685,906 A | | 8/1987 | Murphy |
| 4,733,802 A | | 3/1988 | Sheldon |
| 4,792,334 A | | 12/1988 | Py |
| 4,805,750 A | | 2/1989 | Nitz |
| 4,909,801 A | | 3/1990 | Casey et al. |
| 4,960,407 A | | 10/1990 | Cope |
| 5,007,905 A | | 4/1991 | Bauer |
| D330,418 S | | 10/1992 | Carter |
| 5,207,657 A | | 5/1993 | Gibilsco |
| 5,221,027 A | | 6/1993 | Gibilsco |
| 5,295,981 A | * | 3/1994 | Smith .................. A61F 9/0026 |
| | | | 604/301 |
| 5,497,910 A | | 3/1996 | Meadows |
| 5,578,021 A | | 11/1996 | Cornish |
| 5,611,788 A | | 3/1997 | Marchment |
| 5,902,292 A | | 5/1999 | Feldman |
| 6,033,384 A | | 3/2000 | Py |
| D424,690 S | | 5/2000 | Szabo |
| D426,300 S | | 6/2000 | Conforti |
| D445,178 S | | 7/2001 | Cogger |
| 6,371,945 B1 | | 4/2002 | Sherman |
| 6,423,040 B1 | | 7/2002 | Benktzon et al. |
| 6,508,793 B1 | | 1/2003 | Harrold |
| D498,415 S | | 11/2004 | Schuller |
| D545,203 S | | 6/2007 | Perry |
| D550,355 S | | 9/2007 | Racz |
| D575,643 S | | 8/2008 | Florio |
| D592,957 S | | 5/2009 | David |
| D596,945 S | | 7/2009 | Barnett |
| D604,166 S | | 11/2009 | Gallo |
| D628,490 S | | 12/2010 | Sato et al. |
| D651,903 S | | 1/2012 | Teller |
| 8,216,195 B2 | | 7/2012 | Wu |
| D681,478 S | | 5/2013 | Riffe |
| D758,867 S | | 6/2016 | Tsai |
| 9,763,826 B2 | | 9/2017 | Cooper |
| D820,001 S | | 6/2018 | Cannamela |
| 9,999,540 B2 | | 6/2018 | Yang et al. |
| 10,053,245 B2 | | 8/2018 | Leistner et al. |
| D840,821 S | | 2/2019 | Kokubo |
| D887,845 S | | 6/2020 | LaPierre |
| 11,628,089 B2 | | 4/2023 | Gamboa Burgos |
| D985,396 S | | 5/2023 | Matsubara |
| 11,759,797 B2 | | 9/2023 | Greiner-Perth |
| 11,826,281 B1 | | 11/2023 | Blazevich |
| D1,007,680 S | | 12/2023 | Blazevich |
| 12,070,415 B1 | | 8/2024 | Blazevich |
| D1,045,610 S | | 10/2024 | Blazevich |
| 12,127,978 B1 | | 10/2024 | Blazevich |
| D1,060,662 S | | 2/2025 | Blazevich |
| 2004/0007556 A1 | | 1/2004 | Manera |
| 2005/0101921 A1 | | 5/2005 | Sherman |
| 2007/0045354 A1 | | 3/2007 | Boyd et al. |
| 2007/0073231 A1 | | 3/2007 | Lee |
| 2007/0086507 A1 | | 4/2007 | Kim |
| 2007/0233020 A1 | | 10/2007 | Hearne |
| 2008/0208148 A1 | | 8/2008 | Soon |
| 2010/0145287 A1 | | 6/2010 | Grevin |
| 2012/0310184 A1 | | 12/2012 | Pedersen |
| 2013/0096517 A1 | | 4/2013 | Leistner |
| 2013/0220967 A1 | | 8/2013 | Wang |
| 2014/0350492 A1 | | 11/2014 | Rojas |
| 2015/0351960 A1 | | 12/2015 | Cooper |
| 2016/0038339 A1 | | 2/2016 | Behan |
| 2016/0089526 A1 | | 3/2016 | Hofland |
| 2017/0129659 A1 | | 5/2017 | Spiegelhoff |
| 2019/0127119 A1 | | 5/2019 | Kokubo |
| 2021/0378863 A1 | | 12/2021 | Gamboa Burgos |
| 2022/0151829 A1 | | 5/2022 | Henderson |
| 2024/0091058 A1 | | 3/2024 | Nagel |
| 2024/0409281 A1 | | 12/2024 | Heinzle |

FOREIGN PATENT DOCUMENTS

| | | |
|---|---|---|
| CN | 1129301157 A | 6/2021 |
| ES | 2060969 T3 | 12/1994 |
| ES | 1078238 U | 12/2012 |
| ES | 2529056 T3 | 2/2015 |
| JP | 2012065874 A | 4/2012 |
| JP | 2019217056 A | 12/2019 |
| WO | WO 2020/025515 A1 | 2/2020 |
| WO | WO 2020/080962 A1 | 4/2020 |
| WO | WO 2020/214135 A1 | 10/2020 |

OTHER PUBLICATIONS

Autodrop Eye Drop Guide, Caregiversproducts.com, [Post date: Dec. 5, 2012], [Site seen May 11, 2023], Seen at URL: https://www.caregiverproducts.com/autodrop-eye-drop-guide.html (Year: 2012).

Eye Guide Aid, Eyedrop Bottle Dispenser, first available Dec. 13, 2022, amazon.ca, [online], [site visited Sep. 24, 2024], Available from internet URL: https://www.amazon.ca/dp/BOBPXRM3CH/ (Year: 2022).

International Search Report and Written Opinion for dated Mar. 24, 2025, issued in corresponding PCT Patent Application No. PCT/US2024/057440.

International Search Report and Written Opinion dated Mar. 28, 2025, issued in corresponding PCT Patent Application No. PCT/US2024/057483.

International Search Report for International Application No. PCT/PE2018/000022 dated May 22, 2019.

Moorfields Eye Hospital NHS Foundation Trust, Opticare, Feb. 19, 2019, Youtube Video retrieved Feb. 25, 2025 (Year: 2019).

Opticare Eye Dropper Dispenser, McArthur Medical Sales, [Post date: unknown], [Site seen at URL: https://mmsiestore.com/product/opticare-eye-dropper-dispenser/ (Year: 2023).

Rohoto All-in-One Lubricant redness reliever, rohoto, rohotoeyedrops.com, {Post date: Sep. 30, 2022], {Site seen May 11, 2023], Seen at URL: https://rohtoeyedrops.com/products-rohto-all-in-one-multi-symptom-eye-drops (Year: 2022).

These Japanese Eye Drops Give My Face Instant Energy, first available Mar. 28, 2017, nymag.com, [online], [site visited Sep. 23, 2024], Available from internet URL: https://nymag.com/strategisUarticle/best-eye-drops-for-reducing-redness-rohto-eye-drops-review.html (Year: 2017).

* cited by examiner

EYE DROP DISPENSER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 18/907,367, filed on Oct. 4, 2024, which is a continuation-in-part of U.S. patent application Ser. No. 18/654,342, filed on May 3, 2024, the entire disclosure of both of which is incorporated herein by reference.

FIELD

The present disclosure is directed to an eye drop or eye wash or eye lid cleaner dispenser bottle, and more particularly to an eye drop or eye wash or eye lid cleaner dispenser with an eye cup for dispensing eye drops or eye wash or eye lid cleaner.

DESCRIPTION OF THE RELATED ART

Eye drops are regularly used to treat eye conditions such as dry eye, bacterial infections, eye injury, or eye conditions such as glaucoma and cataracts. Existing eye drop dispensers are deficient in that they do not accurately or consistently deliver the drops into the eye (e.g., affecting children and elderly people more), often delivering the drops on other parts of the user's face, leading to multiple attempts and making the solution difficult to administer. These multiple attempts cause an unnecessary wasting of the eye drops, thereby costing the consumer more. Another deficiency of existing eye drop dispensers is that user's may contaminate existing eye drop dispensers by touching their eye or face with the dispenser causing bacteria to grow on the dispenser tip and leading to eye infections. When the user suffers from hand tremors (e.g., essential tremor disorder or other neurological conditions) which cause shaking hands while trying to deliver the eye drops, the tremors exacerbate the defects of existing eye drop dispensers. Because existing dispenser designs make delivering eyedrops difficult, there is a decrease in compliance by users to take their medication.

SUMMARY

The systems, methods, and devices described herein have innovative aspects, no single one of which is indispensable or solely responsible for their desirable attributes. Without limiting the scope of the claims, some of the advantageous features will now be summarized.

In some aspects, the techniques described herein relate to an eye drop dispenser assembly, including: a dispenser bottle having a circumferential sidewall, a first surface, and a chamber extending between an opening in the first surface and a bottom of the dispenser bottle. The dispenser assembly further including an eye cup fixedly coupled to a second surface of the dispenser bottle, the eye cup having a circumferential sidewall disposed around the chamber, and a distal edge of the circumferential sidewall defining an oval shape, the distal edge configured to be disposed over an eye socket to facilitate delivery of a solution into a user's eye.

In some aspects, the dispenser assembly further including a cap removably couplable to the dispenser bottle over the chamber.

In some configurations, the dispenser bottle also has a shoulder, and the cap is removably couplable to the shoulder.

In some configurations, an outer surface of the cap is tangential to the dispenser bottle.

In some configurations, the dispenser bottle has a recess cavity extending away from the distal edge of the eye cup.

In some configurations, the circumferential wall of the eye cup is partially disposed within the recess cavity.

In some aspects, the techniques described herein relate to an eye drop dispenser assembly, including: a dispenser bottle including a circumferential sidewall, a first surface, and a chamber extending between an opening in the first surface and a bottom of the dispenser bottle. The dispenser assembly further including: a vial having a nipple, wherein the vial is removably disposed within the chamber, and an eye cup fixedly coupled to a second surface of the dispenser bottle, the eye cup having a circumferential sidewall disposed around the chamber, and a distal edge of the circumferential wall defining an oval shape, the distal edge configured to be disposed over an eye socket to facilitate delivery of a solution into a user's eye.

In some configurations, the nipple is aligned with a central axis of eye cup.

In some configurations, the vial is a single-use vial cartridge.

In some configurations, the dispenser assembly has a retention lip extending from the chamber, the retention lip configured to retain the vial in the chamber.

In some configurations, the nipple does not extend past the second surface.

In some configurations, a maximum width and depth of the eye cup is smaller than a maximum width and depth of the dispenser bottle.

The eye cup inhibits the nipple from contacting an eye.

In some configurations, the distal edge of the eye cup is contoured.

In some configurations, the dispenser assembly further includes a cap removably couplable to the dispenser bottle over the nipple, the cap having an outer wall, an inner wall extending within the outer wall, and a seal at or proximal an end of the inner wall.

In some configurations, the inner wall seals the nipple substantially simultaneously with the outer wall coupling to a shoulder of the dispenser bottle.

In some aspects, the techniques described herein relate to an eye drop dispenser assembly, including: a dispenser bottle having a chamber, a coupling mechanism proximate the chamber, a vial having a nipple, the vial removably disposed within the internal chamber, and an eye cup having a first open end and a second open end opposite the first open end and configured to removably fit over at least a portion of the dispenser bottle, the first open end having an oval shape and the second open end having a circular shape, the eye cup being couplable to the coupling mechanism of the dispenser bottle in a stowed position where the eye cup is disposed below the nipple and about the upper portion of the dispenser bottle, the eye cup further being couplable to the coupling mechanism of the dispenser bottle in a deployed position where the eye cup is disposed so that it extends around and distally from the nipple, wherein the eye cup in the deployed position facilitates delivery of eye drops into a user's eye.

In some configurations, the dispenser bottle further comprises an upper portion recessed relative to a lower portion, and wherein an outer surface of the eye cup circumferentially aligns with an outer surface of the lower portion of the dispenser bottle when in the stowed position.

In some configurations, the dispenser bottle has an upper portion between the lower portion and the coupling mechanism, the lower portion having a greater width than the upper portion, the upper portion tapering from the lower portion toward the nipple.

In some configurations, the dispenser bottle further comprises a bottom surface having an opening into the chamber.

In some configurations, the vial is insertable into the chamber via the opening in the bottom surface.

DETAILED DESCRIPTION

Figure 1B:
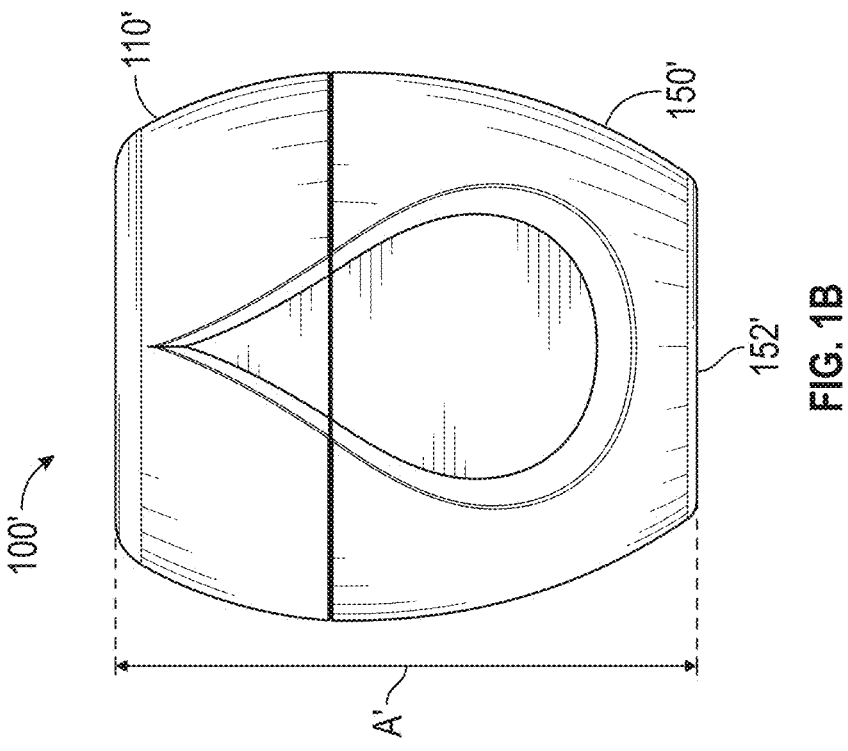
FIG. 1B is a schematic front view of a second embodiment of an eye drop dispenser assembly.

Embodiments of the eye drop dispenser assembly will now be described with reference to the accompanying figures, wherein like numerals refer to like or similar elements throughout. Although several embodiments, examples, and illustrations are disclosed below, it will be understood by those of ordinary skill in the art that the inventions described herein extends beyond the specifically disclosed embodiments, examples, and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

FIGS. 1A, 2A-2C, 4A, 5C and 6A show a dispenser assembly 100 (the "assembly 100"). The assembly 100 includes a dispenser bottle 150 (e.g., dispenser body), an eye cup 140, a nipple 130, and a cap 110. The dispenser bottle 150, the eye cup 140, and/or the cap 110 can optionally be made in part or whole of plastic (e.g., polypropylene), silicone or rubber. In one example, the eye cup 140 can be translucent. In one example, the eye cup 140 can be transparent. However, the dispenser bottle 150, the eye cup 140, and/or the cap 110 can be made of other suitable materials (e.g., flexible or resilient materials). The eye cup 140 may be formed from a clear or transparent material. The dispenser assembly 100 can house and deliver a solution (e.g., eye drops, eye wash, eye lid cleaner and/or wash) onto or over the eye or a portion thereof (e.g., eye lid).

FIGS. 1B, 3A-3C, 4B, 5D, 6B, 7B and 8B show views of a dispenser assembly 100' (hereafter "the assembly 100'"), which is a compact (e.g., small or pocket sized) version of the dispenser assembly 100. The compact dispenser assembly 100' is also referred to as the multi-use assembly 100'. Some of the features of the assembly 100' are similar to features of the assembly 100 in FIGS. 1A, 2A-2C, 4A, 5C and 6A. Thus, reference numerals used to designate the various components of the assembly 100' are identical to those used for identifying the corresponding components of the assembly 100 in FIGS. 1A, 2A-2C, 4A, 5C and 6A, except that a """ has been added to the numerical identifier. Therefore, the structure and description for the various features of the assembly 100 and how it is operated and controlled in FIGS. 1A, 2A-2C, 4A, 5C and 6A are understood to also apply to the corresponding features of the assembly 100', except as described below. The dispenser assembly 100' can house and deliver a solution (e.g., eye drops, eye wash, eye lid cleaner and/or wash) onto or over the eye or a portion thereof (e.g., eye lid).

The dispenser assembly 100 includes a dispenser bottle 150 with a base 152 and a cap 110 removably couplable to an end of the dispenser bottle 150 opposite to (e.g., distal from) the base 152. In some embodiments, the base 152 is flat. In other embodiments, a portion, but less than all, of the base 152 is flat. The base 152 allows the dispenser bottle 150 to stand upright when not in use which advantageously reduces the amount of fluid (e.g., eye drops, eye wash, eye lid cleaner and/or wash) wasted. The cap 110 is removably coupled to the dispenser bottle 150. The assembly 100 has a height A measured from the base 152 to a top of the cap 110. In one implementation, the height A is between about 2 and 3 inches, such as 2.5 inches.

The dispenser assembly 100' includes a dispenser bottle 150' (e.g., dispenser body) with a base 152' and a cap 110' removably couplable to an end of the dispenser bottle 150' opposite to (e.g., distal from) the base 152'. In some embodiments, the base 152' is flat. In other embodiments, a portion, but less than all, of the base 152' is flat. The assembly 100' has a height A' measured from the base 152' to a top of the cap 110'. In one implementation, the height A' is between about 1.5 and 2.5 inches, such as 2 inches. In one example, the eye cup 140' can be translucent. In one example, the eye cup 140' can be transparent.

Figure 1A:
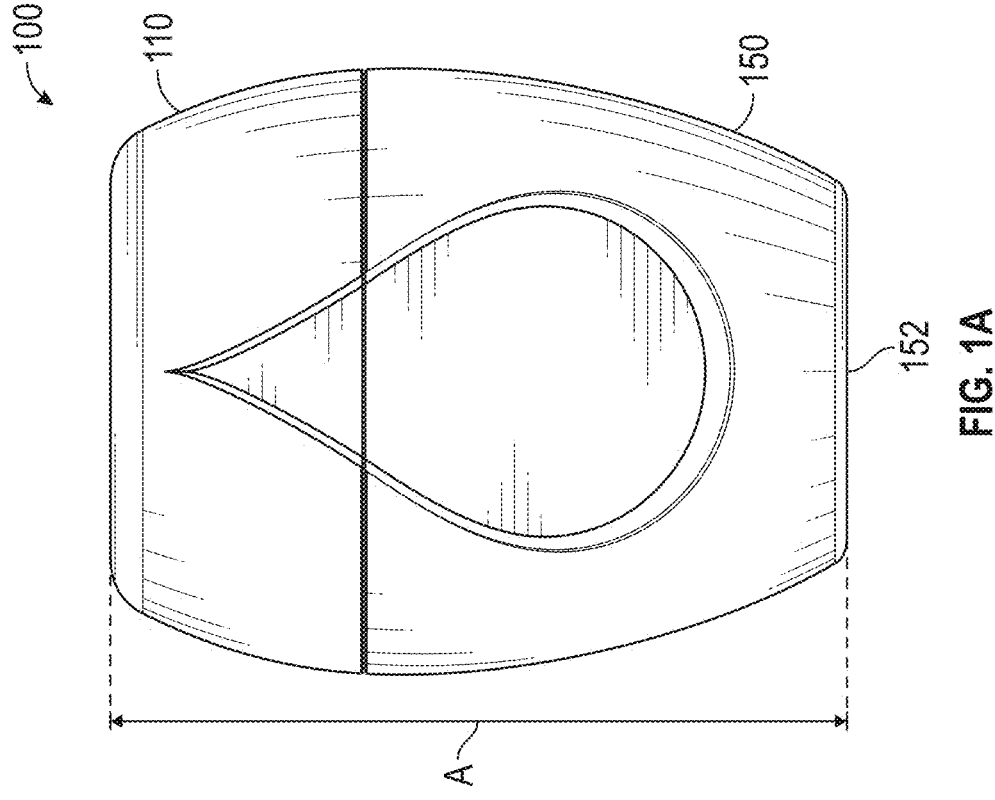
FIG. 1A is a schematic front view of one embodiment of an eye drop dispenser assembly.
Figure 2A:
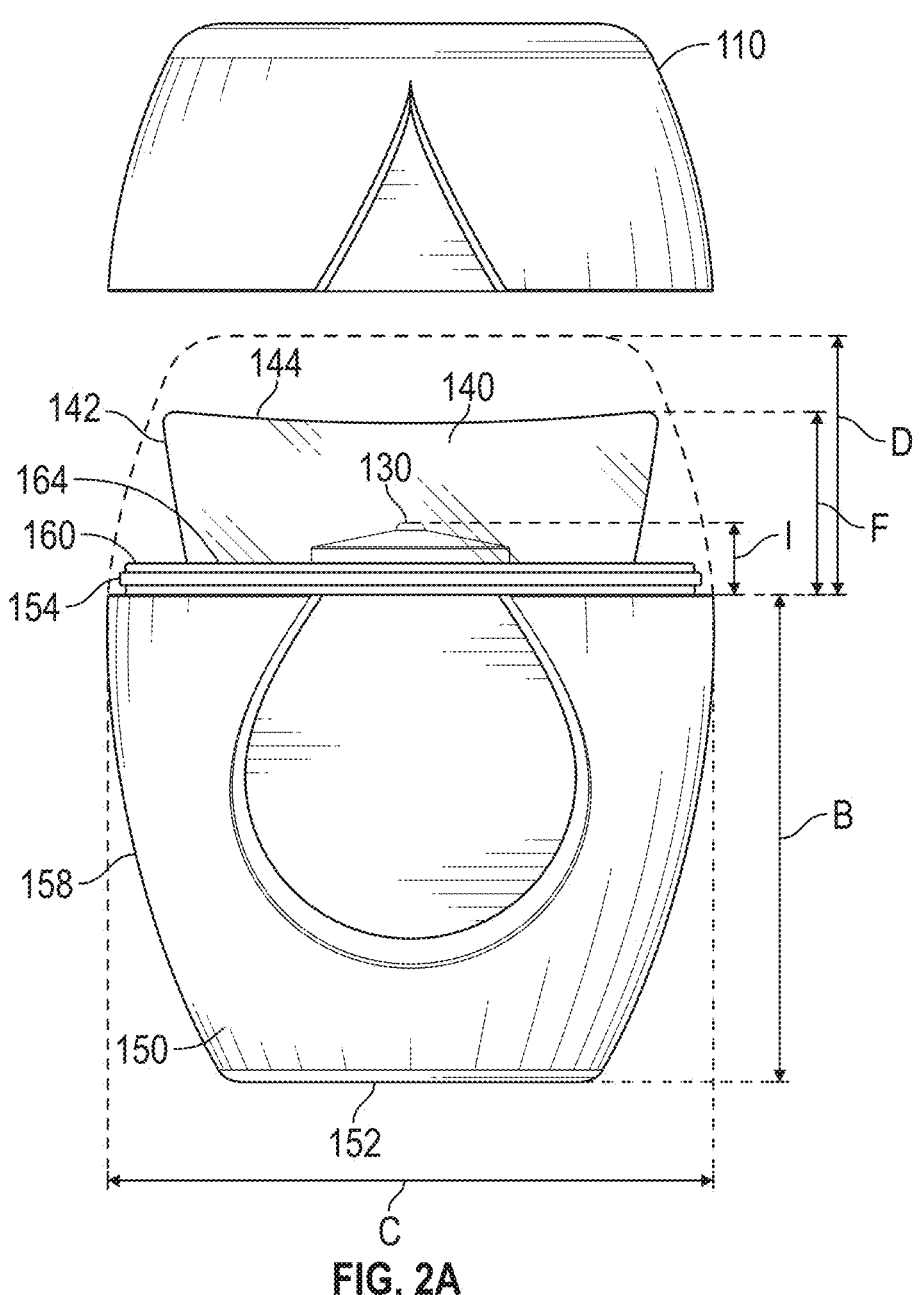
FIG. 2A is a schematic front view of the eye drop dispenser assembly of FIG. 1A with its cap removed and spaced above the dispenser bottle, the dashed line showing the outline of the cap when covering the eye cup.

FIG. 2A depicts a front view of the dispenser assembly 100 shown in FIG. 1A with the cap 110 removed. The dispenser bottle 150 has the base 152 connected to a side wall 158. The side wall 158 is circumferential and extends from the base 152. The dispenser bottle 150 has a nipple 130 projecting from a surface 164 of the dispenser bottle 150 that is at an opposite end of the dispenser bottle 150 (e.g., distal) from the base 152. The nipple 130 can be centered relative to the dispenser bottle 150. The nipple 130 can have a circular profile, as shown for example in FIG. 4A; however, the nipple 130 can have other suitable shapes. In some embodiments, the circumferential side wall 158 can flex (e.g., when the dispenser bottle 150 is squeezed). The dispenser bottle 150 also has a shoulder 154 that circumscribes a second surface 160. The second surface 160 connect to the circumferential side wall 158. In the illustrated embodiment the surface 164 is coplanar with the second surface 160. The cap 110 is removably couplable to the dispenser bottle 150 around the shoulder 154. In some examples the cap 110 is removably couplable to the shoulder 154 with an annular snap-fit. In some embodiments, the shoulder 154 is disposed to extend above the second surface 160. In other embodiments, the shoulder 154 is formed integral to the second surface 160 (e.g., the second surface 160 forms the upper surface of the shoulder 154 such that when the cap 110 is on, or connects to, the second surface 160 fits within the cap 110 rather than the cap 110 sitting on the second surface 160). In the illustrated arrangement, the assembly 100 also includes an eye cup 140 integrated with the dispenser bottle 150, which provides a supporting structure to the dispenser bottle 150 when it is inverted for delivery of solution on or over the eye (e.g., the eye cup 140 resting on the user's eye socket to support the dispenser bottle 150 in the inverted position). The eye cup 140 is coupled to the second surface 160 of the dispenser bottle 150 (e.g., to an end of the dispenser bottle 150 opposite the base 152). The eye cup 140 can fit within the cap 110 when the cap 110 is coupled to the dispenser bottle 150. In some embodiments, the eye cup 140 is fixedly coupled to the second surface 160 (e.g., so that the eye cup 140 is integral to, and cannot be detached or removed from, the dispenser bottle 150). The eye cup 140 has a circumferential wall 142 that extends to an edge 144 that is distal to the dispenser bottle 150. In one example, the eye cup 140 (e.g., the circumferential wall 142) tapers toward the second surface 160. The circumferential wall 142 defines an oval shape surrounding the nipple 130 (e.g., when the dispenser assembly 100 is viewed from the top with the cap 110 removed, see FIG. 4A. The circumferential wall 142 surrounds the nipple 130, and the nipple 130 is disposed between the distal edge 144 of the circumferential wall and the second surface 160 of the dispenser bottle 150.

The dispenser bottle 150 can optionally be made of plastic, silicone, rubber, or other suitable resilient or flexible material. The dispenser bottle 150 can optionally be a single piece (e.g., a monolithic, seamless single piece). In some embodiments, the base 152, side wall 158, surface 164, second surface 160, shoulder 154, nipple 130, and eye cup 140, or any combination thereof, may be formed as a single piece. The single piece can be an integrated assembly of several parts or can be a unitary structure formed from a single piece of material. In some embodiments, the base 152, side wall 158, surface 164, second surface 160, shoulder 154, nipple 130, and eye cup 140 may be made from plastic, rubber, silicone or any suitable material. Any of these portions may be made from the same material or from different materials.

In the illustrated arrangement, the assembly 100 has a width C. In one implementation, the width C is between 1.5 and 2.5 inches, such as 2 inches. The dispenser bottle 150 has a height B measured from the base 152 to the surface 164. In one implementation, the height B is between 1.25 and 2 inches, such as 1.625 inches. The dispenser bottle 150 also has a height I measured from the surface 164 to the top of the nipple 130. The assembly 100 has a height F measured from the second surface 160 to the distal edge 144. Height F is advantageously larger than height I to inhibit (e.g., prevent) the nipple 130 from contacting the eye 300 when in use. This positioning advantageously prevents (e.g., inhibits) contamination of the nipple 130 or injury to the eye 300 during use. Additionally, in some examples the height I may be less than half of height F which advantageously further reduces the chance that the nipple 130 will inadvertently touch the user's eye 300 or otherwise be contaminated. In other embodiments, the height I may be greater than half the height F. In one implementation, the height I is between 0 and 0.4 inches, such as 0.2 inches and the height F is between 0.25 and 0.75 inches, such as 0.5 inches. The assembly 100 also has a height D. Height D is the height of the cap 110. In one implementation, height D is greater than height F. In one implementation, the height D is between 0.5 and 1.0 inches, such as 0.875 inches.

Figure 2B:
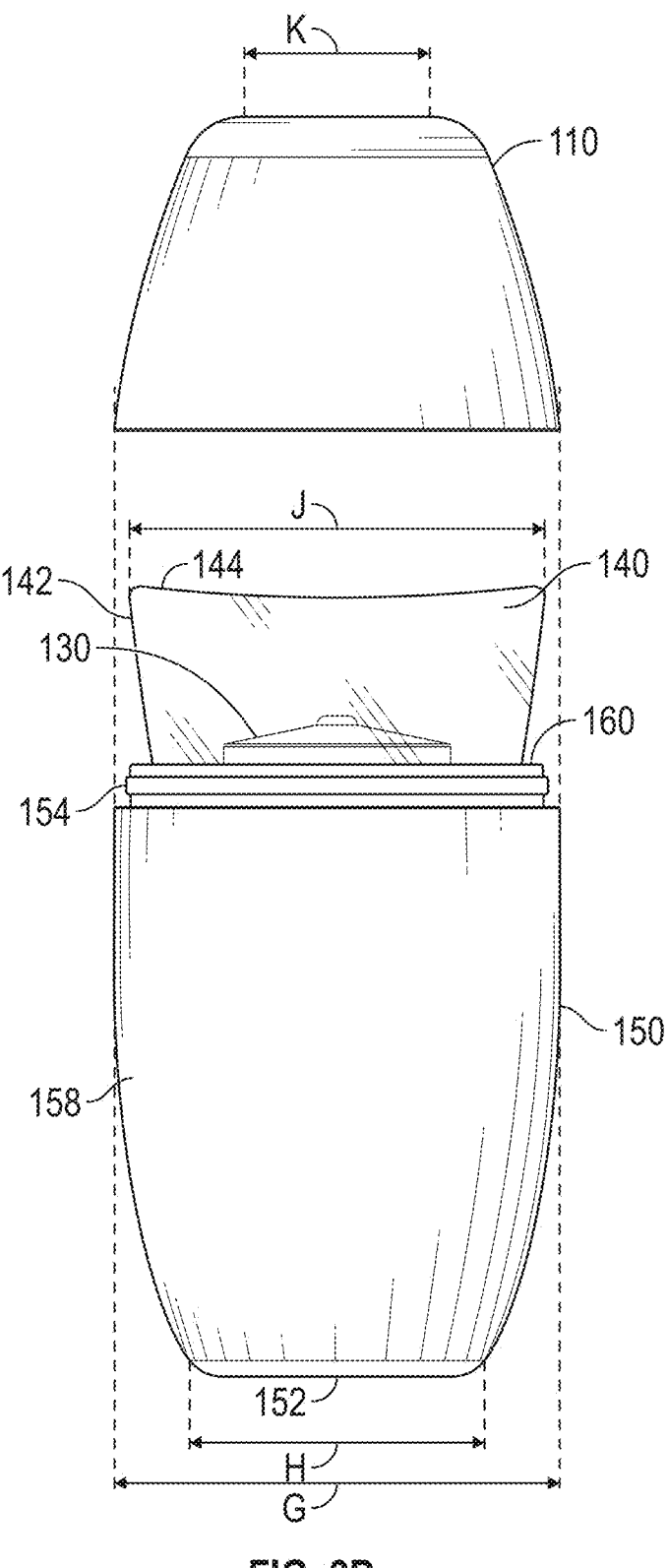
FIG. 2B is a schematic side view of the eye drop dispenser assembly of FIG. 1A with its cap removed and spaced above the dispenser bottle.

With reference to FIG. 2B, the assembly 100 has a depth G. The base 152 has a depth H. Depth G may be larger than depth H. In one implementation, the depth G is between 1 and 1.5 inches, such as 1.25 inches and the depth H is between 0.5 and 1 inch, such as 0.75 inches. The eye cup 140 has a depth J. Depth J may be smaller than Depth G. In one implementation, the depth J is between 1 and 1.25 inches, such as 1.1 inches. The cap 110 has a depth K (at its distal end). In one implementation, the depth K is between 0.5 and 0.75 inches, such as 0.7 inches.

Figure 2C:
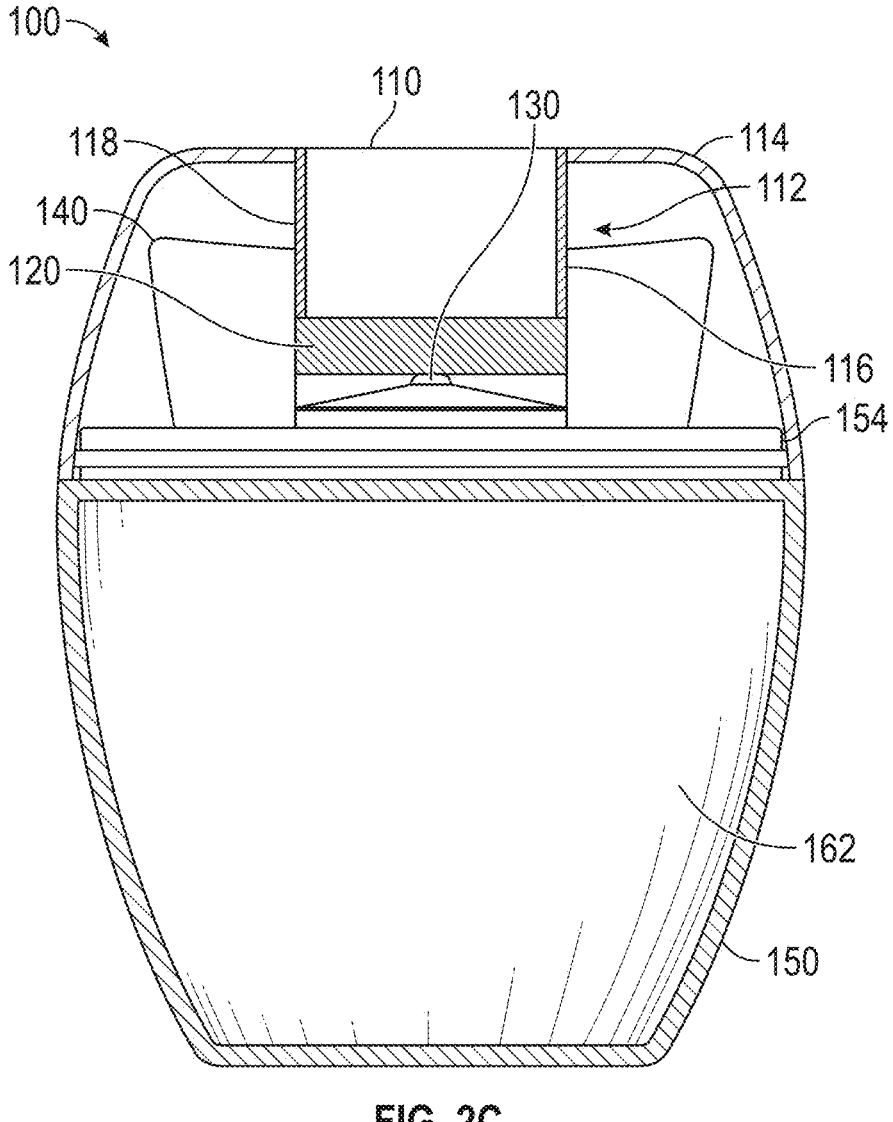
FIG. 2C is a schematic cross-sectional view of the eye drop dispenser assembly of FIG. 1A, where the section line is through the midplane of the side view in FIG. 2B.

FIG. 2C depicts a cross-sectional view of the dispenser assembly 100 shown in FIG. 2A. The section is taken at a midpoint of the depth G of the assembly 100 (see FIG. 2B). The dispenser bottle 150 has a chamber 162 that can hold a liquid solution (e.g., eye drop solution, eye wash solution, eye lid cleaner or wash solution). The cap 110 is connected to the dispenser bottle 150. The eye cup 140 fits within a cavity 112 of the cap 110 when the cap 110 is removably coupled to the dispenser bottle 150. The cap 110 has an outer wall 114 that defines the cavity 112. Within the cavity 112, is a post 118 extending from an underside of the outer wall 114. In one example, the post 118 is solid. In another example, the post 118 includes a hollow portion (e.g., at a distal end of the post 118). The post 118 has a seal 120 at its distal end. In one example, the seal 120 is separate from the post 118 and is disposed within the hollow portion of the post 118. In another example, the seal 120 is separate from the post 118 and is attached to an end of the post 118. In another example, the seal 120 is integral (e.g., one piece, monolithic) with the post 118 (e.g., the seal 120 is a distal portion of the post 118 and made of the same or similar material as the post 118). When the cap 110 is coupled to the dispenser bottle 150, the outer wall 114 is coupled to (e.g., disposed around) the shoulder 154 of the dispenser bottle 150. The post 118 and the seal 120 define an inner wall 116 that is coupled to (e.g., disposed around) the nipple 130 so that a distal portion of the post 118 encircles the nipple 130 and is coupled to the nipple 130. The seal 120 sits adjacent the top of the nipple 130 and presses against the nipple 130 to inhibit (e.g., prevent) leakage of solution from the nipple 130. In another example, when the cap 110 is coupled to the dispenser bottle 150, the seal 120 at the end of the post 118 engages (e.g., contacts) the nipple 130 to inhibit (e.g., prevent) leakage of solution from the dispenser bottle 150. In one example, the seal 120 can have a shape similar to (e.g., a mirror image of) a shape of the nipple 130). The post 118 is disposed within the eye cup 140 when the cap 110 is connected to the dispenser bottle 150 (e.g., when the cap 110 is coupled to the dispenser bottle 150 the post 118 is surrounded by the eye cup 140, which is surrounded by the outer wall 114).

Figure 3A:
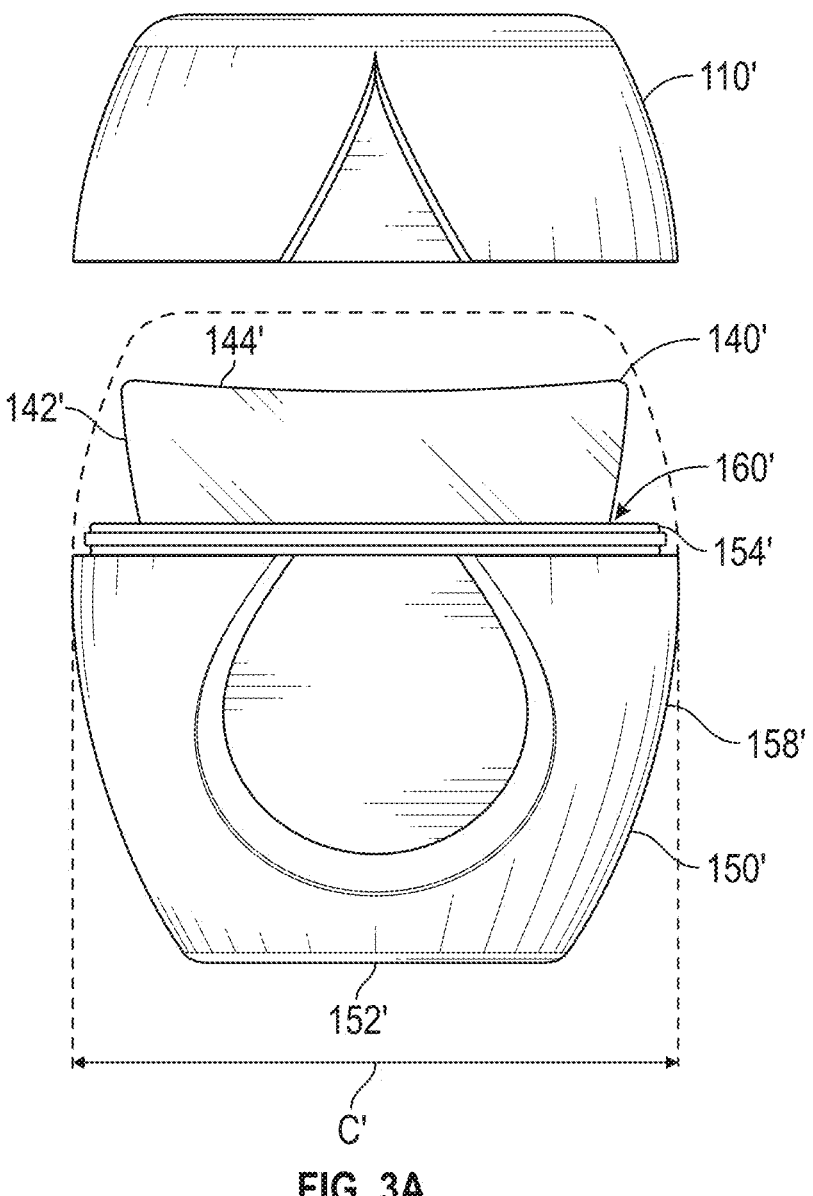
FIG. 3A is a schematic front view of the eye drop dispenser assembly of FIG. 1B with its cap removed and spaced above the dispenser bottle, the dashed line showing the outline of the cap when covering the eye cup.

FIG. 3A depicts a front view of the dispenser assembly 100' shown in FIG. 1B with the cap 110' removed. The assembly 100' has a dispenser bottle 150 having a base 152' connected to a side wall 158'. The dispenser bottle 150' has a nipple 130' projecting from a surface 164' (e.g., a recessed surface shown in FIG. 3C) of the dispenser bottle 150' that is at an opposite end of the dispenser bottle 150' (e.g., distal) from a base 152'. The nipple 130' can have a circular profile, as shown for example in FIG. 4B; however, the nipple 130' can have other suitable shapes. The dispenser bottle 150' also has a shoulder 154' circumferential to a second surface 160' and distal to the base 152', as shown in FIG. 3A. The side wall 158' also connected to the second surface 160'. In some embodiments, the shoulder 154' is disposed to extend above the second surface 160'. In other embodiments, the shoulder 154' is formed integral to the second surface 160' (e.g., the second surface 160' forms the upper surface of the shoulder 154' such that when the cap 110' is on, the second surface 160' fits within the cap 110' rather than the cap 110' sitting on the second surface 160'). The second surface 160' is parallel to the base 152'. In the illustrated arrangement, shown in FIG. 3C, the assembly 100' also includes an eye cup 140'. The eye cup 140' is fixedly coupled or integrated to the dispenser bottle 150'. When the cap 110' is coupled to the dispenser bottle 150', the eye cup 140' can fit within the cap 110'. The eye cup 140' has a circumferential wall 142' and an edge 144' (e.g., a top edge) that is distal to the dispenser bottle 150'. In one example, the eye cup 140' (e.g., the circumferential wall 142') tapers toward the second surface 160'.

With reference to FIG. 3A, the assembly 100' has a width C'. In one implementation, the width C' is between 1.5 and 2.5 inches, such as 1.9 inches.

Figure 3B:
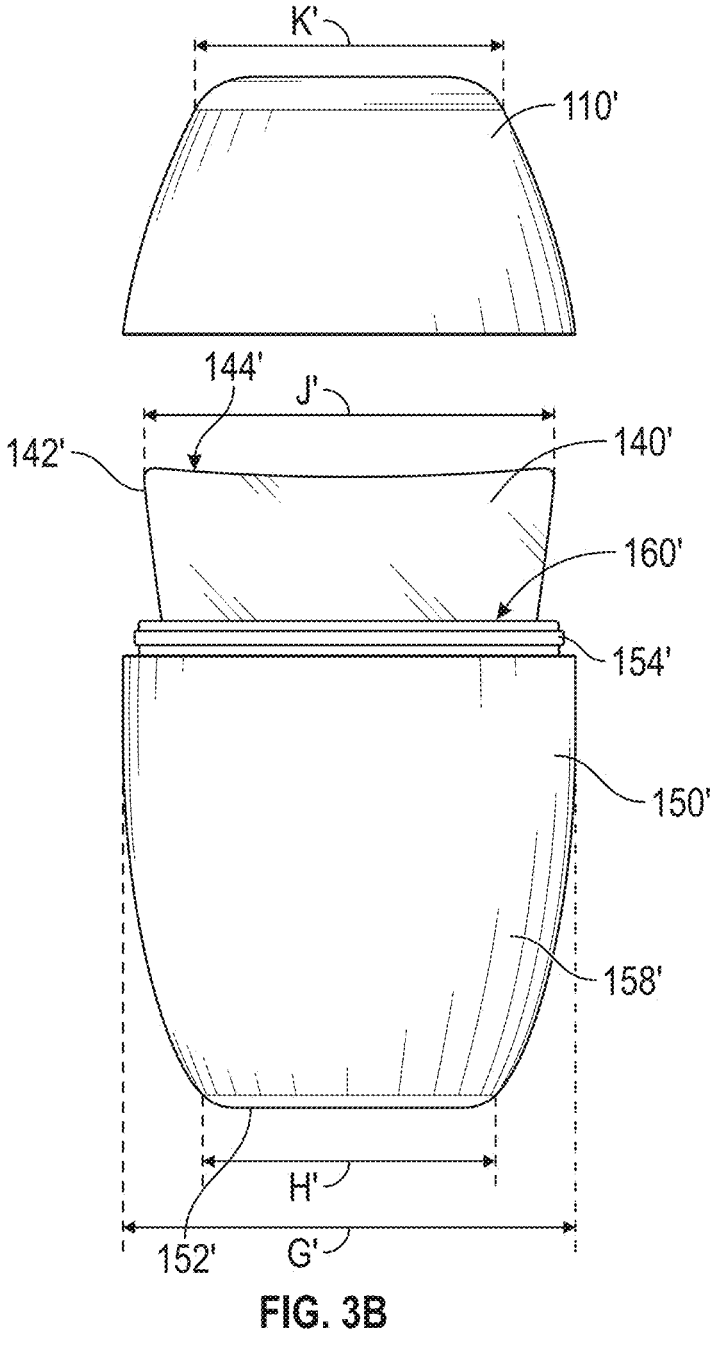
FIG. 3B is a schematic side view of the eye drop dispenser assembly of FIG. 1B with its cap removed and spaced above the dispenser bottle.

With reference to FIG. 3B, the assembly 100' has a depth G'. The base 152' has a depth H'. Depth G' may be larger than depth H'. In one implementation, the depth G' is between 1 and 1.75 inches, such as 1.2 inches or 1.4 inches and the depth H' is between 0.5 and 1 inches, such as 0.8 inches. The eye cup 140' has a depth J'. Depth J' may be smaller than Depth G'. In one implementation, the depth J' is between 1 and 1.5 inches, such as 1.1 inches or 1.25 inches. The cap 110' has a depth K' (at its distal end). In one implementation, the depth I' is between 0.5 and 1 inches, such as 0.9 inches or 0.75 inches.

Figure 3C:
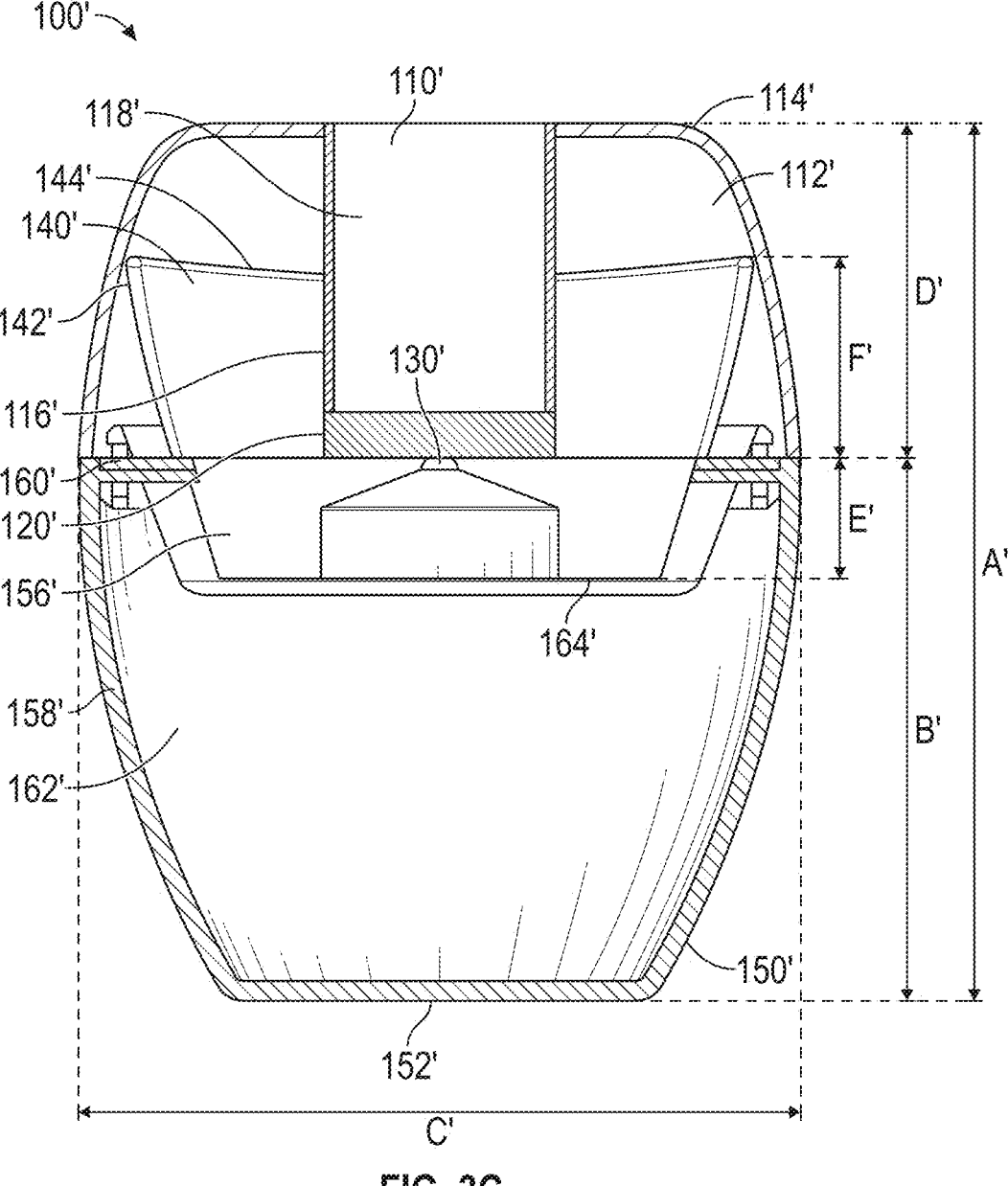
FIG. 3C is a schematic cross-sectional view of the eye drop dispenser assembly of FIG. 1B, where the section line is through the midplane of the side view in FIG. 3B.

FIG. 3C depicts a cross-sectional view of the dispenser assembly 100' shown in FIG. 3A. The section is taken at a midpoint of the depth G' of the assembly 100' (see FIG. 3B). The dispenser bottle 150' has a chamber 162' that can hold a liquid. The cap 110' is connected to the dispenser bottle 150'. The dispenser bottle 150' has a nipple 130' projecting from a surface 164'. The surface 164' is between the second surface 160' and the base 152'. The positioning of the surface 164' creates a recess cavity 156' around the nipple 130'. The recess cavity 156' extends into the dispenser bottle 150' and away from the distal edge 144' of the eye cup 140'. The positioning of the recess cavity 156' allows the nipple 130' to be recessed proximal (e.g., the nipple 130' is nested in the recess cavity 156' of the dispenser bottle 150') to the dispenser bottle 150' while projecting towards the distal edge 144' of the eye cup 140', allowing the dispenser assembly 100' to be more compact than the dispenser assembly 100. The eye cup 140' fits within a cavity 112' of the cap 110' and the circumferential wall 142' defines an oval shape surrounding the nipple 130'. The nipple 130' is disposed between distal edge 144' of the circumferential wall 142' and the surface 164' of the dispenser bottle 150'. In one example, the circumferential wall 142' is partially disposed within the recess cavity 156'. The cap 110' has an outer wall 114' that defines the cavity 112'. Within the cavity 112', is a post 118' extending from the outer wall 114'. In one example, the post 118' is solid. In another example, the post 118' includes a hollow portion (e.g., at a distal end of the post 118'). The post 118' has a seal 120' at its distal end. In one example, the seal 120' is separate from the post 118' and is disposed within the hollow portion (e.g., distal hollow portion) of the post 118'. In another example, the seal 120' is separate from the post 118' and is attached to an end of the post 118'. In another example, the seal 120' is integral (e.g., one piece, monolithic) with the post 118' (e.g., the seal 120' is a distal portion of the post 118' and made of the same or similar material as the post 118'). The outer wall 114' is disposed around the shoulder 154' of the bottle 150'. The post 118' and the seal 120' define an inner wall 116'. The seal 120' sits adjacent the top of the nipple 130' and presses against the nipple 130' to inhibit leakage of a solution or liquid from the nipple 130'. In one example, the seal 120' can have a shape similar to (e.g., a mirror image of) a shape of the nipple 130'). The post 118' is disposed within the eye cup 140' when the cap 110' is connected to the dispenser bottle 150'.

In the illustrated arrangement, the bottle 150' has a height B' measured from the base 152' to the second surface 160'. In one implementation, the height B' is between 1 and 1.75 inches, such as 1.25 inches or 1.5 inches. The assembly 100' has a height F' (for the eye cup 140') measured from the surface 164' to the distal edge 144'. In one example, the eye cup 140' extends from the second surface 160' (e.g., the eye cup 140' is outside the recess cavity 156'). In another example, the eye cup 140' extends from the surface 164' so that at least a portion of the circumferential wall 142' of the eye cup 140' is in the recess cavity 156' of the bottle 150'. In one implementation, the height F' is between 0.25 and 0.75 inches, such as 0.4 inches or 0.5 inches. The assembly 100' also has a height D'. Height D' is the height of the cap 110'. The height D' is greater than height F'. In one implementation, the height D' is between 0.5 and 1 inches, such as 0.75 inches or 0.9 inches. The dispenser bottle 150' has a height E' measured from the second surface 160' to the surface 164' (e.g., the bottom surface of the recess cavity 156'). In one implementation, the height E' is between 0.1 and 0.6 inches, such as 0.25 inches or 0.6 inches. In some arrangements, the second surface 160' may be coplanar with the surface 164' and height E' is zero inches. In some examples, the second surface 160' and the surface 164' can be portions of the same surface.

Figures 4A, 4B:
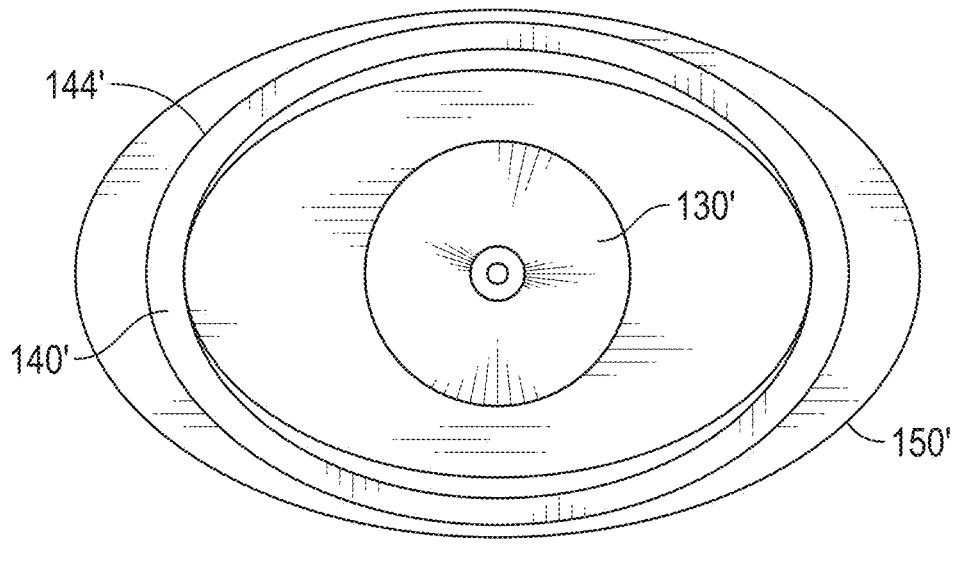
FIG. 4A is a schematic top view of the eye drop dispenser assembly of FIG. 1A.
FIG. 4B is a schematic top view of the eye drop dispenser assembly of FIG. 1B.

FIG. 4A depicts a top view of the assembly 100. The dispenser bottle 150 is shown with the distal edge 144 of the eye cup 140 having an oval shape and disposed around the nipple 130. In this embodiment, the dispenser bottle 150, has an oval shaped perimeter. In other implementations, the perimeter of the dispenser bottle 150 or eye cup 140 may take different forms (e.g. substantially polygonal, or substantially circular).

FIG. 4B depicts a top view of the assembly 100'. The dispenser bottle 150' is shown with the distal edge 144' of the eye cup 140' having an oval shape and disposed around the nipple 130'. The nipple 130' is centered relative to the eye cup 140' and the dispenser bottle 150'. In this embodiment, the dispenser bottle 150', has an oval shaped perimeter. In other implementations, the perimeter of the dispenser bottle 150' or eye cup 140' may take different forms (e.g. substantially polygonal, or substantially circular).

Figure 5A:
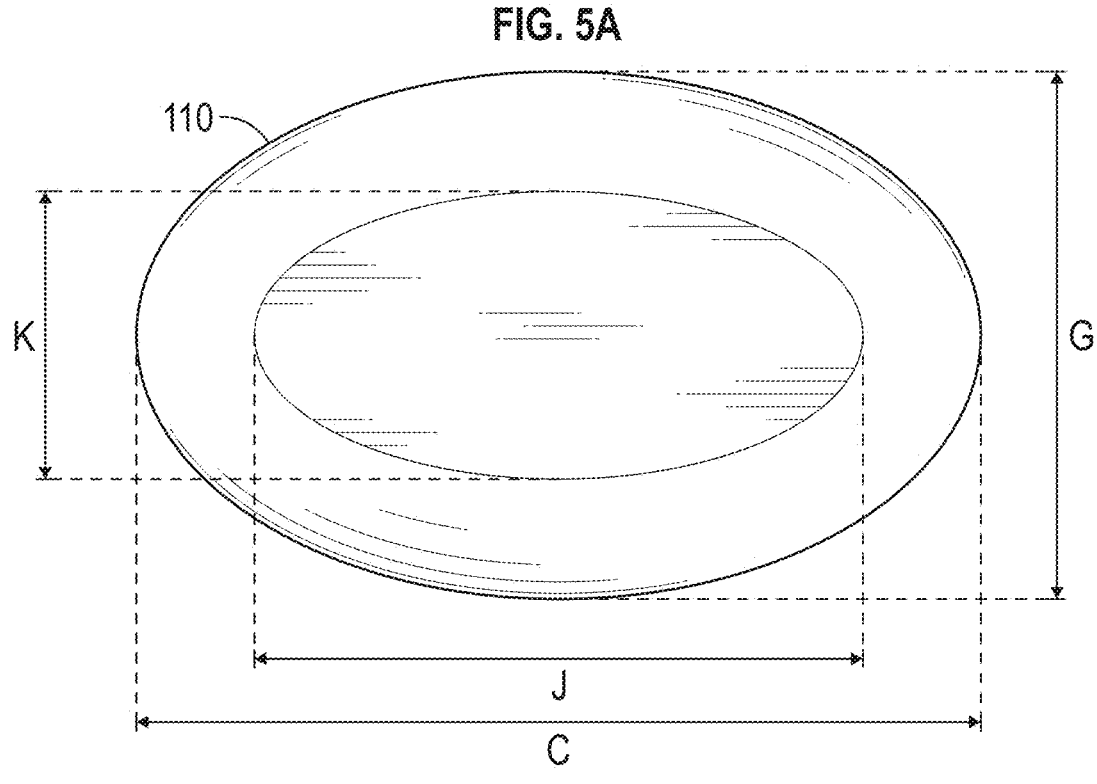
FIG. 5A is a schematic top view of the cap of the eye drop dispenser assembly of FIG. 1A and FIG. 1B.
Figure 5B:
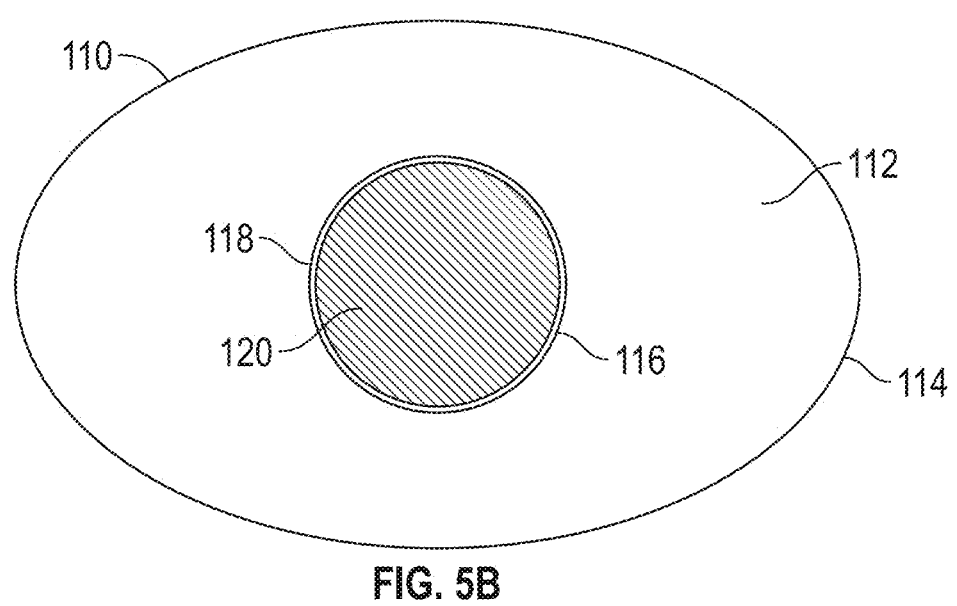
FIG. 5B is a schematic bottom view of the cap of FIG. 5A.
Figure 5C:
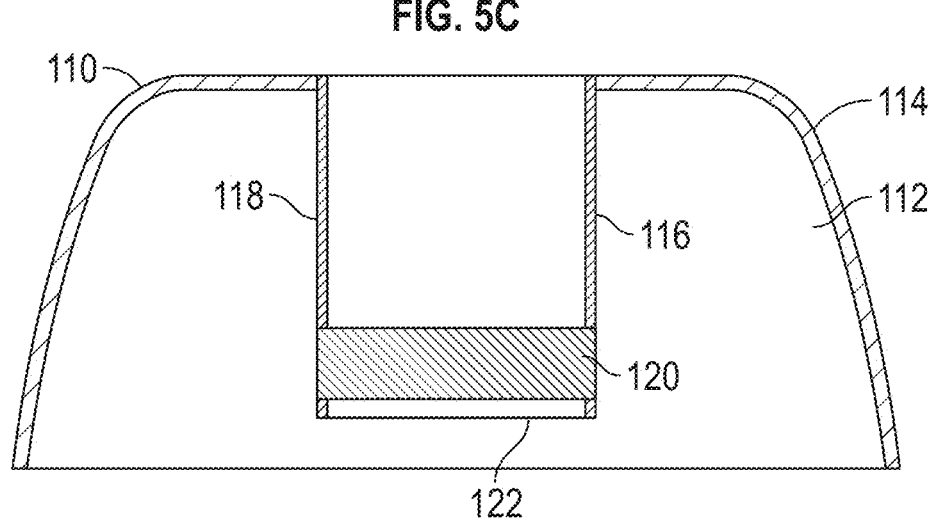
FIG. 5C is a schematic cross-sectional view of the front view of one embodiment of the cap of FIG. 5A, where the section line is through the midplane of the side view.
Figure 5D:
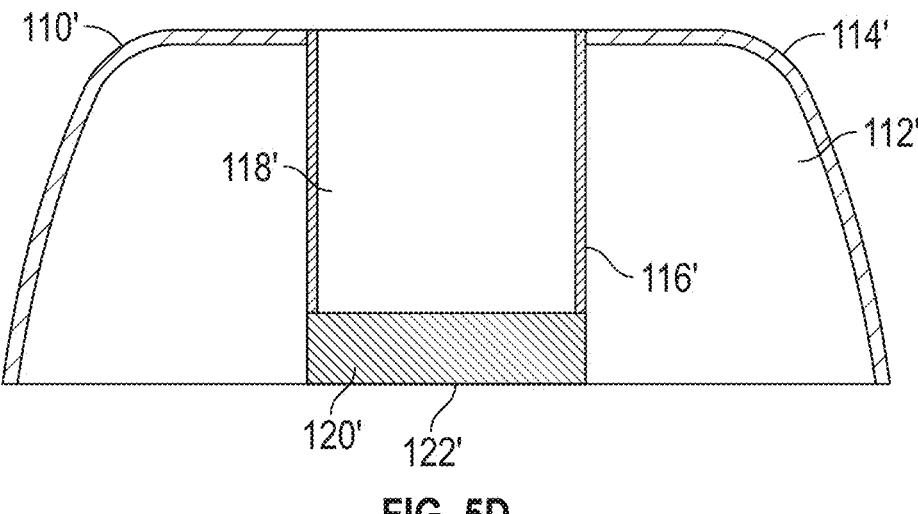
FIG. 5D is a schematic cross-sectional view of the front view of a second embodiment of the cap of FIG. 5A, where the section line is through the midplane of the side view.

FIGS. 5A-5D depict the cap 110. FIG. 5A depicts a top view of the cap 110 and FIG. 5B depicts a bottom view of the cap 110. It is understood that this illustration can be either of the embodiments shown in FIGS. 1A and 1B. FIG. 5C depicts a cross-sectional front view of one embodiment of the cap 110 and FIG. 5D depicts a cross-sectional front view of another embodiment of the cap 110'. It is understood that FIGS. 5A and 5B may depict either the embodiment in 5C or the embodiment in 5D.

In the arrangement illustrated in FIG. 5A, the cap 110 has an oval shaped perimeter. In other implementations, the perimeter of the cap 110 may take different forms (e.g., substantially polygonal, or substantially circular). The perimeter of the cap 110 has width C and a depth G. In one implementation, the width C is between 1.5 and 2.5 inches, such as 2 inches and the depth G is between 1 and 1.5 inches, such as 1.25 inches. The top of the cap 110 has a substantially flat surface with an oval shaped perimeter. The perimeter has a width J and a depth K. In one implementation, the width J is between 1.2 and 1.6 inches, such as 1.4 inches and the depth K is between 0.5 and 1 inches, such as 0.7 inches.

FIG. 5B depicts the bottom view of the arrangement illustrated in FIG. 5A. The cap 110 has an outer wall 114, an inner wall 116 extending within the outer wall 114, and a seal 120 recessed in the inner wall 116. The outer wall 114 defining a cavity 112 and the inner wall 116 defined by a post 118.

FIG. 5C depicts a cross-sectional front view of one embodiment of the cap 110. In this embodiment, the post 118 extends into the cavity 112 and the seal 120 sits within the post 118. In one example, a distal portion 122 of the post 118 extends past the seal 120.

FIG. 5D depicts a cross-sectional front view of a second embodiment of the cap 110'. In this embodiment, the post 118' extends into the cavity 112' and the seal 120' sits within the post 118'. The seal 120' extends to the extent of the post 118' (e.g., the seal 120' is at the distal end 122' of the post 118') and the post 118' extends to the extent of the cavity 112'.

In some embodiments, the outer wall 114, the inner wall 116, and the seal 120, or any combination thereof, may be formed as a single piece. The single piece can be an integrated assembly of several parts or can be a unitary structure formed from a single piece of material. In some embodiments, the seal 120, the outer wall 114, and the inner wall 116 may be made from metal, plastic, rubber, or any suitable material. Any of these portions may be made from the same material or from different materials.

Figure 6A:
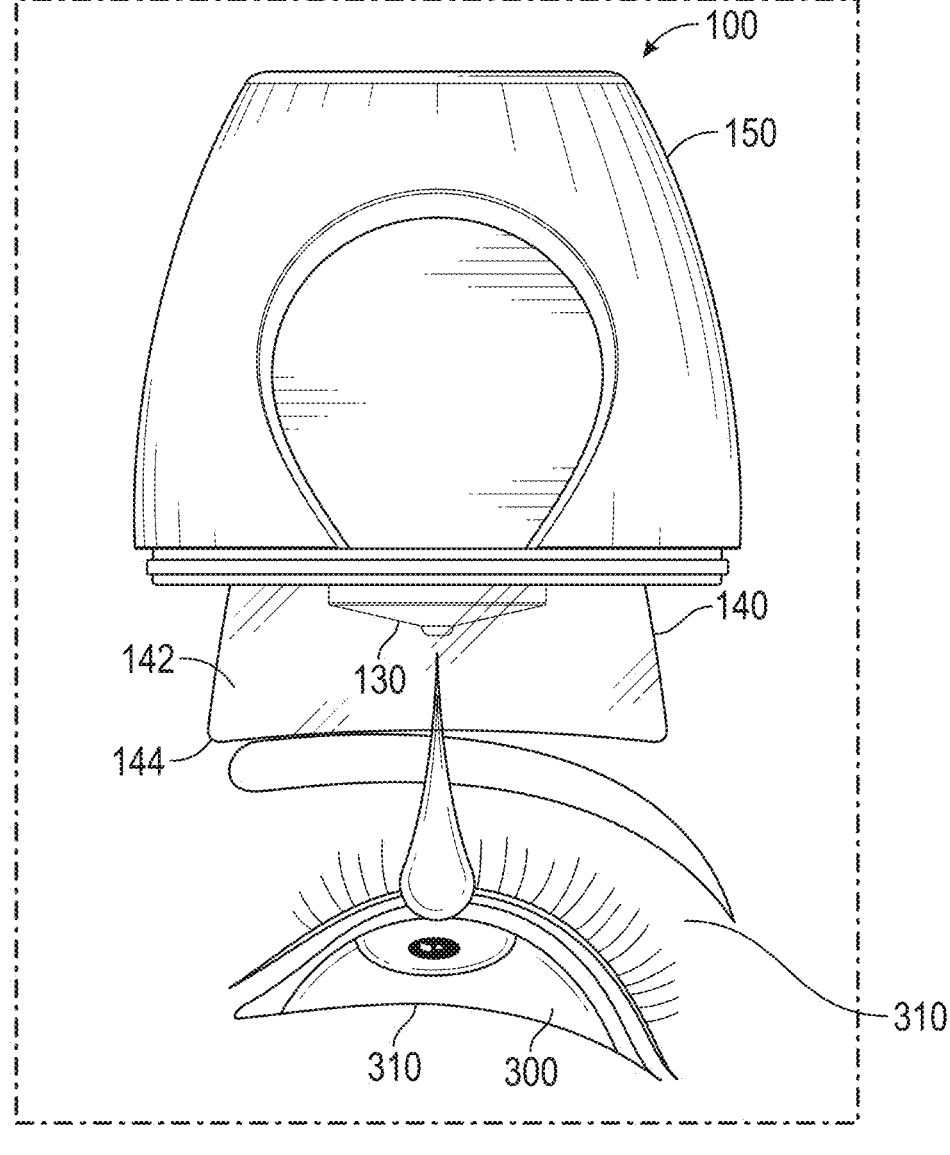
FIG. 6A is a schematic view of the eye drop dispenser of FIG. 1A in an inverted position over a user's eye to deliver an eye drop thereto.
Figure 6B:
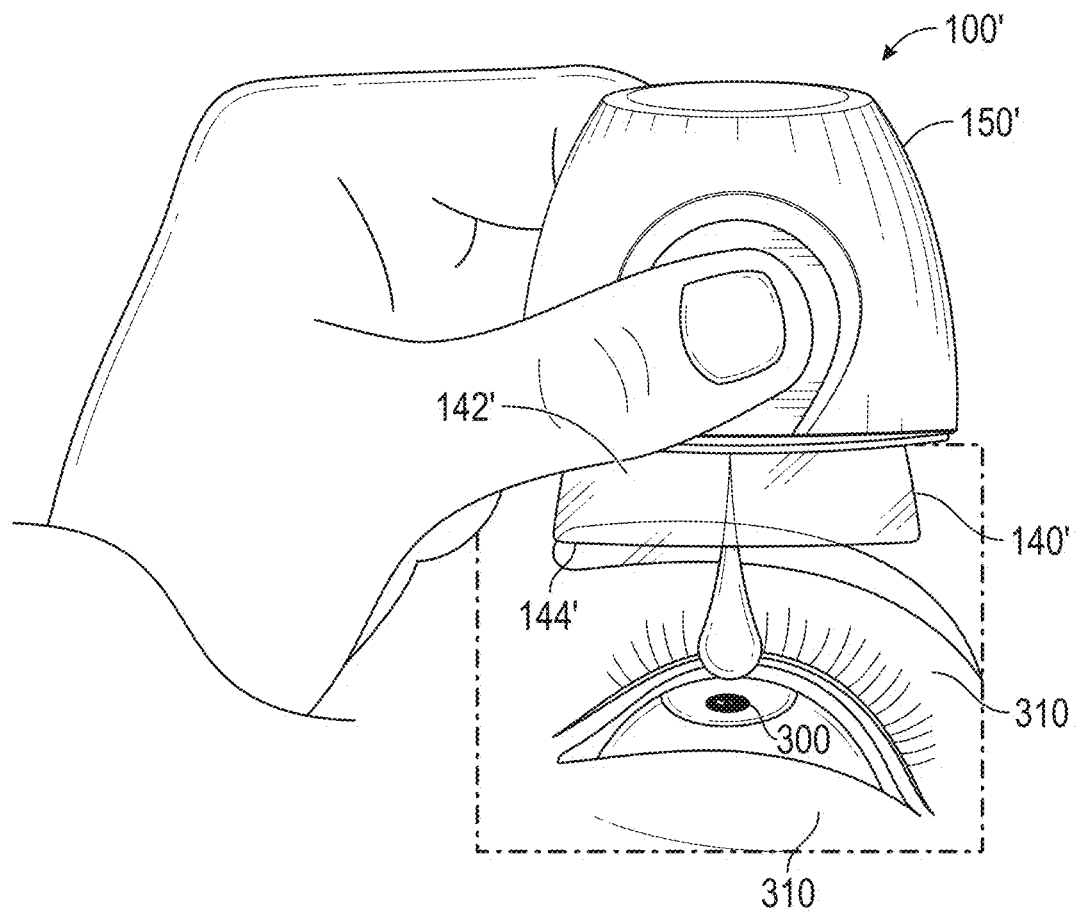
FIG. 6B is a schematic view of the eye drop dispenser of FIG. 1B in an inverted position over a user's eye to deliver an eye drop thereto.

As shown in FIG. 6A, the assembly 100 can be inverted and disposed over an eye 300 so that the eye cup 140 is disposed over (e.g., in contact with) an eye socket 310 of the eye 300 (e.g., to that the eye cup 140 provides a supporting structure that supports the dispenser bottle 150 in an inverted position on the eye socket 310 of the user's eye 300). The user can then squeeze the dispenser bottle 150 to dispense one or more drops into the eye 300. This arrangement advantageously facilitates self-administration of a solution to a user's eye 300 and is user friendly as it does not require the user to assemble the eye cup onto the bottle and can apply it with one hand. Rather, the user simply removes the cap 110 from the dispenser bottle 150, inverts the dispenser bottle 150, places the eye cup 140 against the eye socket 310 of the eye 300, and squeezes the dispenser bottle 150 to dispense the solution. Further, the nipple 130 is advantageously centered relative to the eye cup 140 (e.g., aligned with a central axis of the eye cup 140) so that when the eye cup 140 is supported on the eye socket 310, the nipple 130 is generally aligned (e.g., centered) relative to the eye 300, further ensuring the dispensed solution will be delivered onto or over the eye 300. Advantageously, the eye cup 140 is sized to dispose the distal edge 144 over (e.g., in contact with) the periorbital region 310 and align the nipple 130 with the center of the eye 300. The distal edge 144 of the eye cup 140 is contoured to fit around the periorbital region 310, advantageously allowing the eye cup 140 to comfortably sit or rest over the eye socket 310. This positioning facilitates alignment of the nipple 130 with the eye 300 allowing for dispensing the eye drop(s) directly into the eye 300. This positioning limits (e.g., prevents) waste from having the eye drops fall on the user's face, cheek, eyebrow, ear, etc. Though FIG. 6A depicts the use of the assembly 100, the assembly 100' can be used in the same manner and the advantages listed above also apply to the assembly 100'. This is best illustrated in FIG. 6B.

The contour of the distal edge 144 is defined by two axes. The first axis is defined by the nipple 130 such that the distal edge 144 is contoured circumferentially around the nipple 130. The second axis is defined by a point in space approximating the centroid of the external curvature of a user's periorbital region 310. The distal edge 144 is contoured relative to this axis such that the eye cup 140 fits against the user's face. The ability of the eye cup 140 to sit or rest over the periorbital region 310 advantageously facilitates use of the eye drop dispenser assembly 100 by a user with hand tremors, nervous disorders or children to dispense eye drops into the eye. Additionally, supporting (e.g., sitting or resting) the eye cup 140 over the eye socket 310 can inhibit (e.g., prevent) injury to the eye during delivery of eye drops and inhibit the nipple 130 from touching the user's eye 300, thereby inhibiting (e.g., preventing) contamination of the eye 300.

Figure 7A:
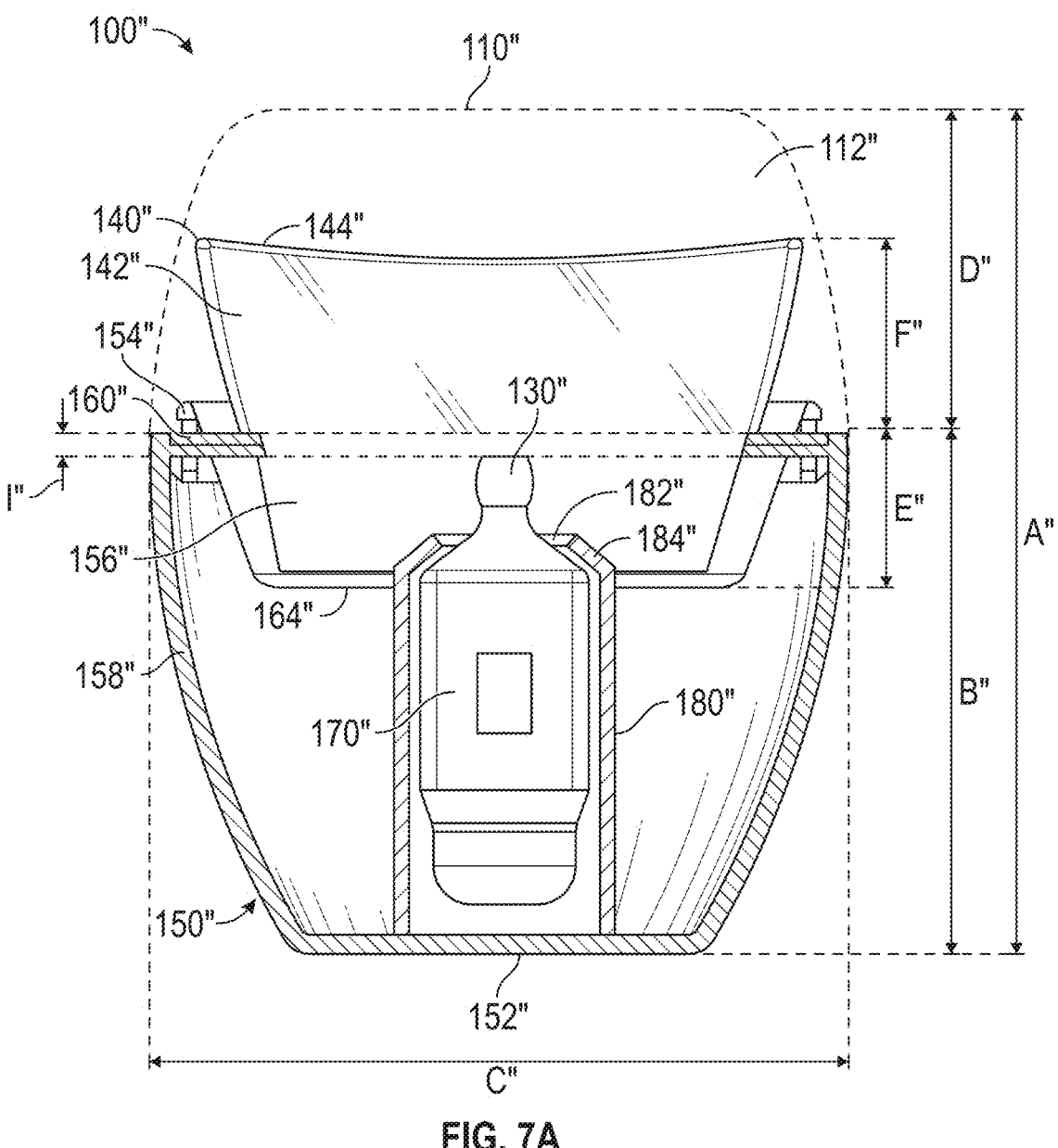
FIG. 7A is a schematic cross-sectional view of the front view of a third embodiment of the eye drop dispenser assembly.
Figures 8A, 8B:
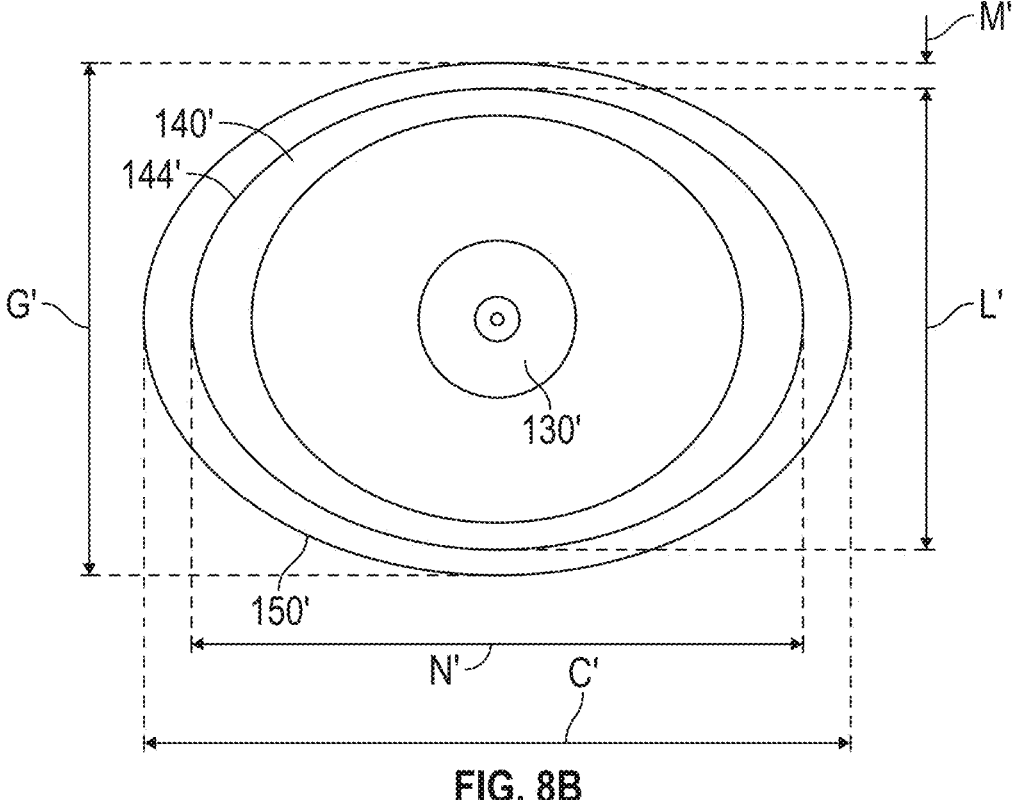
FIG. 8A is a schematic top view of the eye drop dispenser assembly of FIG. 7A.
FIG. 8B is a schematic top view of the eye drop dispenser assembly of FIG. 7B.

FIGS. 7A and 8A show views of a dispenser assembly 100" (hereafter "the assembly 100""), which is a version of the dispenser assembly 100' designed for use with single-use vial cartridges. Some of the features of the assembly 100" are similar to features of the assembly 100' in FIGS. 1B, 3A-3C, 4B, 5D, and 8B. Thus, reference numerals used to designate the various components of the assembly 100" are identical to those used for identifying the corresponding components of the assembly 100' in FIGS. 1B, 3A-3C, 4B, 5D, and 8B, except that a "″" has been added to the numerical identifier. Therefore, the structure and description for the various features of the assembly 100' and how it is operated and controlled in FIGS. 1B, 3A-3C, 4B, 5D, and 8B are understood to also apply to the corresponding features of the assembly 100", except as described below. The dispenser assembly 100" can house and deliver a solution (e.g., eye drops, eye wash, eye lid cleaner and/or wash) onto or over the eye or a portion thereof (e.g., eye lid).

FIG. 7A depicts a cross-sectional front view of a third embodiment of the eye drop dispenser assembly 100". This is the single-use vial cartridge eye drop dispenser assembly 100". The dispenser assembly 100" includes a dispenser bottle 150" (e.g., dispenser body) with a base 152". Additionally, the cap 110' described above can attach to the dispenser bottle 150" in substantially the same way the cap 110' attaches to the dispenser bottle 150'. The cap 110' can be removably couplable to an end of the dispenser bottle 150" opposite to (e.g., distal from) the base 152". In some embodiments, the base 152" is flat. In other embodiments, a portion, but less than all, of the base 152" is flat. The assembly 100" has a height A″ measured from the base 152" to a top of the cap 110'. In one implementation, the height A′ is between about 1.5 and 2.5 inches, such as 2 inches. In one example, the eye cup 140" can be translucent. In one example, the eye cup 140" can be transparent.

The section is taken at a midpoint of the depth G″ of the assembly 100" (see FIG. 8A). The dispenser bottle 150" has a chamber 180" that can hold a single-use vial cartridge 170". FIGS. 7A, 8A shows a single-use vial cartridge 170" inserted into the chamber 180". The single-use vial cartridge 170" is (removably) inserted into the chamber 180" from the bottom of the dispenser bottle 150" (e.g., the end of the dispenser bottle 150" opposite the eye cup 140") and it is held in the chamber 180" (e.g., by friction, such as via a press-fit connection). In some embodiments, the single-use vial cartridge 170" can be a single-use vial. In some embodiments the single-use vial cartridge 170" can be a single-use eye drop vial. The chamber 180" has an opening 182" positioned within the surface 164". The opening 182" can include a retention lip 184" which can hold the single-use vial cartridge 170" in place. The dispenser bottle 150" can be squeezed to dispense fluid from the single-use vial cartridge 170". For example, flexing the dispenser bottle 150" can cause the chamber 180" flex and press on the single-use vial cartridge 170", thereby releasing fluid from the single-use vial cartridge 170". The retention lip 184" can be a snap-fit which allows the single-use vial cartridge 170" to be inserted or removed but retains the single-use vial cartridge 170" in its position while in use. In another implementation, the retention lip 184" can be resilient (e.g., act as a spring to allow insertion of the single-use vial cartridge 170" into the chamber 180" and removal of the single-use vial cartridge 170" from the chamber 180"). The nipple 130" is integral to the single-use vial cartridge 170". The nipple 130" can extend out of the surface 164" (e.g., out of the opening 182"). The surface 164" is between the second surface 160" and the base 152". The positioning of the surface 164" creates a recess cavity 156" around the nipple 130". The recess cavity 156" extends into the dispenser bottle 150" and away from the distal edge 144" of the eye cup 140". The positioning of the recess cavity 156" allows the nipple 130" to be recessed proximal (e.g., the nipple 130" is nested in the recess cavity 156" of the dispenser bottle 150") to the dispenser bottle 150" while projecting towards the distal edge 144" of the eye cup 140", allowing the dispenser assembly 100" to be more compact than the dispenser assembly 100. The eye cup 140" fits within a cavity 112' of the cap 110' and the circumferential wall 142" defines an oval shape surrounding the nipple 130". The nipple 130" is disposed between distal edge 144" of the circumferential wall 142" and the surface 164" of the dispenser bottle 150". In one example, the circumferential wall 142' is partially disposed within the recess cavity 156".

Similar to the description above with regard to FIG. 3C, the outer wall 114' can also be disposed around the shoulder 154" of the bottle 150". The outer wall 114' can be tangential to the outer surface of the dispenser bottle 150". The seal 120' can sit adjacent the top of the nipple 130" and presses against the nipple 130" to inhibit leakage of a solution or liquid from the nipple 130". In one example, the seal 120' can have a shape similar to (e.g., a mirror image of) a shape of the nipple 130"). The post 118' is disposed within the eye cup 140" when the cap 110' is connected to the dispenser bottle 150".

In the illustrated arrangement, the bottle 150" has a height B″ measured from the base 152" to the second surface 160". In one implementation, the height B″ is between 1 and 1.75 inches, such as 1.25 inches or 1.5 inches. The assembly 100" has a height F″ (for the eye cup 140") measured from the surface 164" to the distal edge 144". In one example, the eye cup 140" extends from the second surface 160" (e.g., the eye cup 140" is outside the recess cavity 156"). In another example, the eye cup 140" extends from the surface 164" so that at least a portion of the circumferential wall 142" of the eye cup 140" is in the recess cavity 156" of the bottle 150". In one implementation, the height F'" is between 0.25 and 0.75 inches, such as 0.4 inches or 0.6 inches. The assembly 100" also has a height D'". Height D'" is the height of the cap 110'. The height D'" is greater than height F'". In one implementation, the height D'" is between 0.5 and 1 inches, such as 0.75 inches or 0.9 inches. The dispenser bottle 150" has a height E'" measured from the second surface 160" to the surface 164" (e.g., of the recess cavity 156"). In one implementation, the height E'" is between 0.1 and 0.6 inches, such as 0.25 inches or 0.4 inches. In some arrangements, the second surface 160" may be coplanar with the surface 164" and height E'" is zero inches. In some examples, the second surface 160" and the surface 164" can be portions of the same surface. The single-use dispenser bottle 150" has a height I'" measured from the nipple 130" to the second surface 160". In one implementation the height I'" is between 0'" and 0.1 inches, such as 0.05 inches.

Figure 7B:
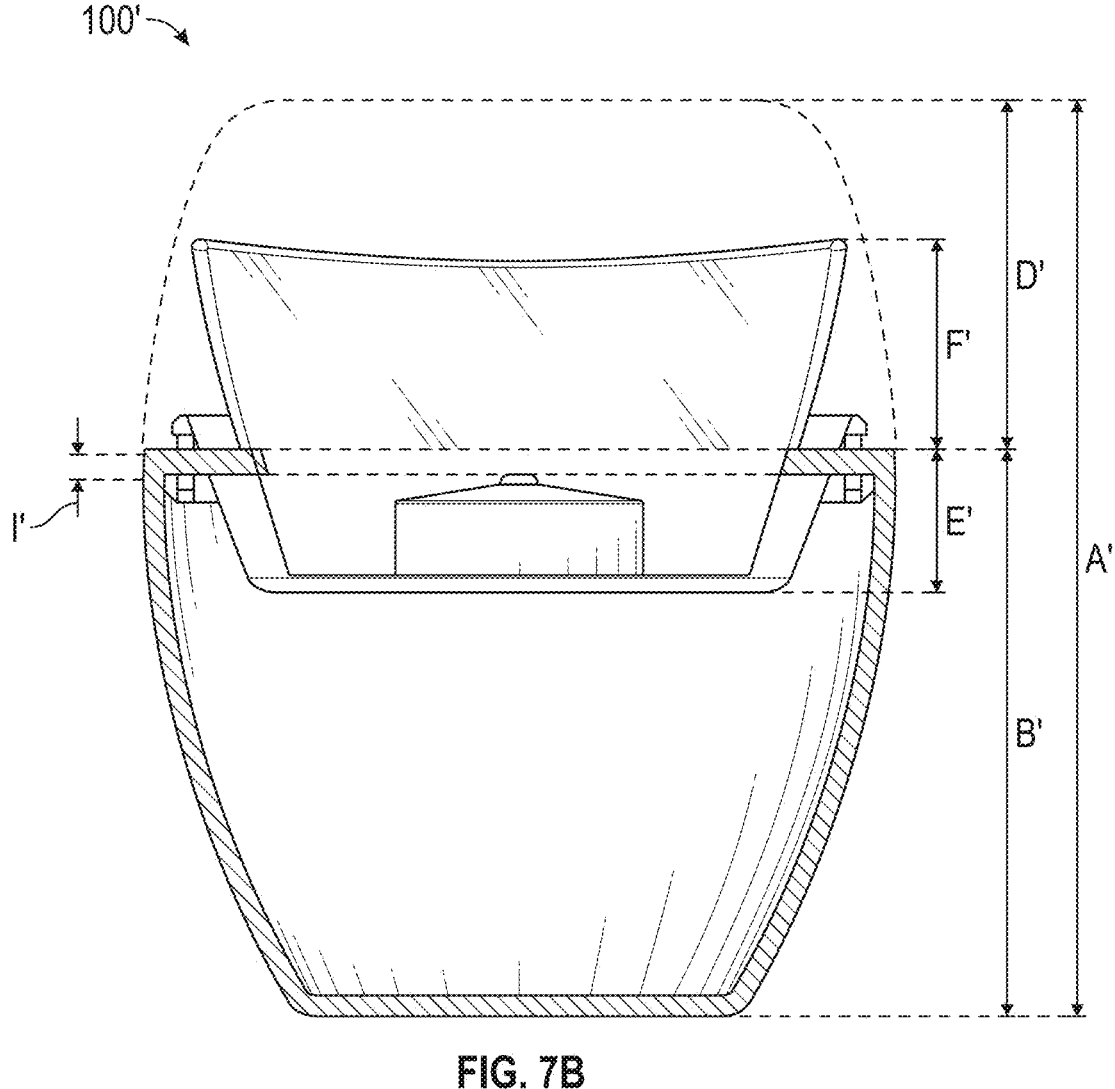
FIG. 7B is a schematic cross-sectional view of the front view of the second embodiment of the eye drop dispenser assembly.

FIG. 7B illustrates a front section view of the eye drop dispenser assembly 100'. As illustrated, the dispenser bottle 150' has a height I' measured from the nipple 130' to the second surface 160'. In one implementation the height I' is between 0 and 0.1 inches, such as 0.05 inches. As discussed above regarding FIG. 3C, the bottle 150' has a height B' measured from the base 152' to the second surface 160'. In one implementation, the height B' is between 1 and 1.75 inches, such as 1.25 inches or 1.5 inches. The assembly 100' has a height F' (for the eye cup 140') measured from the surface 164' to the distal edge 144'. In one implementation, the height F' is between 0.25 and 0.75 inches, such as 0.4 inches or 0.5 inches. The assembly 100' also has a height D'. Height D' is the height of the cap 110'. In one implementation, the height D' is between 0.5 and 1 inches, such as 0.75 inches or 0.9 inches. The dispenser bottle 150' has a height E' measured from the second surface 160' to the surface 164' (e.g., the recessed cavity of the dispenser bottle). In one implementation, the height E' is between 0.1 and 0.6 inches, such as 0.25 inches or 0.4 inches. The overall height A' from the bottom of the dispenser bottle 150' to the top of the cap 110' is the sum of heights B' and D' or between 1.5 inches and 2.75 inches.

FIG. 8A illustrates a top view of the eye drop dispenser assembly 100" of FIG. 7A. The dispenser bottle 150" is shown with the distal edge 144" of the eye cup 140" having an oval shape and disposed around the nipple 130". In this embodiment, the dispenser bottle 150", has an oval shaped perimeter. The nipple 130" is centered relative to the eye cup 140" and the dispenser bottle 150". In other implementations, the perimeter of the dispenser bottle 150" or eye cup 140" may take different forms (e.g. substantially polygonal, or substantially circular). In this embodiment, the single-use vial cartridge 170" is held in place by a retention lip 184".

As illustrated, the dispenser bottle 150" has a depth G" and the eye cup 140" has a depth L". In one implementation, the depth L" is less than the depth G". In one implementation, the depth G" is between 1.25 inches and 1.75 inches, such as 1.4 inches. In one implementation, the depth L" is between 1.0 inches and 1.5 inches such as 1.25 inches. As illustrated, the dispenser bottle 150" has a width C" and the eye cup 140" has a width N". In one implementation, the width C" is greater than the width N". In one implementation, the width C" is between 1.5 and 2.5 inches, such as 1.9 inches. In one implementation, the width N" is between 1.4 inches and 1.8 inches, such as 1.6 inches.

FIG. 8B illustrates a top view of the eye drop dispenser assembly 100' of FIG. 1B. As illustrated, the dispenser bottle 150' has a depth G' and the eye cup 140' has a depth L'. In one implementation, the depth L' is less than the depth G'. In one implementation, the depth G' is between 1 and 1.5 inches, such as 1.2 inches or 1.4 inches. In one implementation, the depth L' is between 1.0 inches and 1.5 inches such as 1.25 inches. As illustrated the dispenser bottle 150' has a width C' and the eye cup 140' has a width N'. In one implementation, the width N' is less than the width C'. In one implementation, the width C' between is 1.5 and 2.5 inches, such as 1.9 inches. In one implementation, the width N' is between 1.4 inches and 1.8 inches, such as 1.6 inches.

Figure 8C:
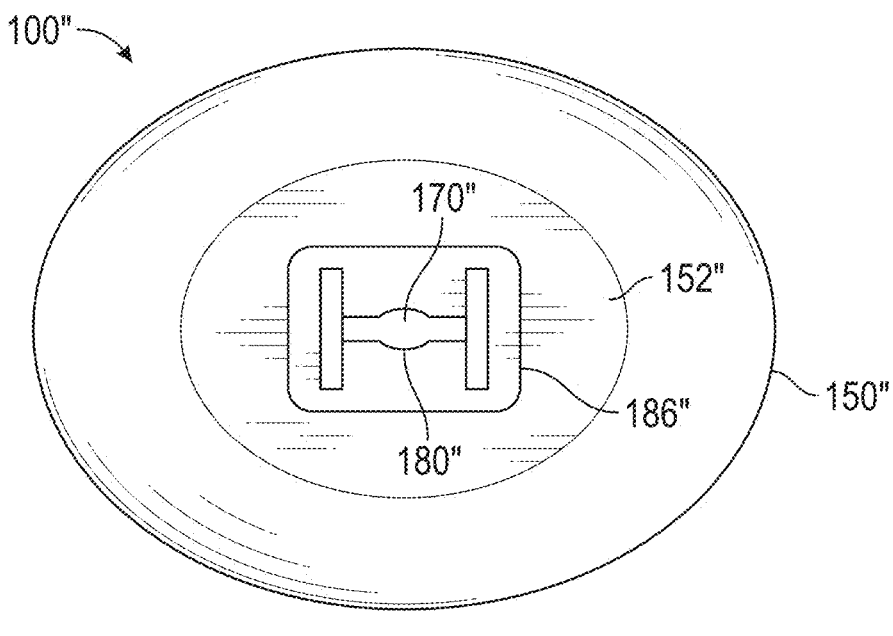
FIG. 8C is a schematic bottom view of the eye drop dispenser assembly of FIG. 7A.

FIG. 8C illustrates a bottom view of the dispenser assembly 100". As illustrated, the base 152" of the dispenser bottle 150" has an opening 186" which opens into the chamber 180". The single-use vial cartridge 170" can be inserted through the opening 186" and into the chamber 180" of the dispenser bottle 150".

The assembly 100' differs from the assembly 100 in that the dispenser assembly 100' has a smaller external envelope. This is accomplished by recessing the nipple 130' as depicted in FIG. 3C. This allows height D' to be less than height D and height A' to be less than height A. Bottle 150 can hold a larger volume of fluid than bottle 150'.

The assembly 100" differs from the assembly 100 in that the dispenser assembly 100" has a smaller external envelope. This is accomplished by recessing the nipple 130" as depicted in FIG. 7A. This allows height D'" to be less than height D and height A'" to be less than height A.

The assembly 100, 100' is advantageously easy to use (e.g., it is easy to remove the cap 110, 110', position the eye cup 140, 140' over the eye 300, and dispense drops in the optimal location without contaminating the nipple 130, 130'). For example, because the eye cup 140, 140' is integrated (e.g., fixed) with the dispenser bottle 150, 150', the user can simply remove the cap 110, 110', invert the dispenser bottle 150, 150' and position it over (e.g., in contact with) their eye socket 310 and squeeze the dispenser bottle 150, 150' to dispense the solution from the dispenser bottle 150, 150'. Additionally, the fixed eye cup 140, 140' advantageously reduces the likelihood that the eye cup 140, 140' will be lost, used improperly, or that the nipple 130, 130' will be or get contaminated.

The assembly 100" is advantageously easy to use (e.g., it is easy to remove the cap 110', insert a single-use vial cartridge 170", remove the top of the single-use vial cartridge 170", position the eye cup 140" over the eye 300, and dispense drops in the optimal location without contaminating the nipple 130") or touching the nipple 130" to the eye 300. This facilitates safe, user-friendly, self-administration of eye drops to a user's eye 300. For example, because the eye cup 140" is integrated (e.g., fixed) with the dispenser bottle 150", the user can simply remove the cap 110, 110', invert the dispenser bottle 150" and position it over (e.g., in contact with) their eye socket 310 and squeeze the dispenser bottle 150" to dispense the solution from the dispenser bottle 150", thereby facilitating self-administration of the eye solution by a user without needing assistance from someone else.

Figure 9A:
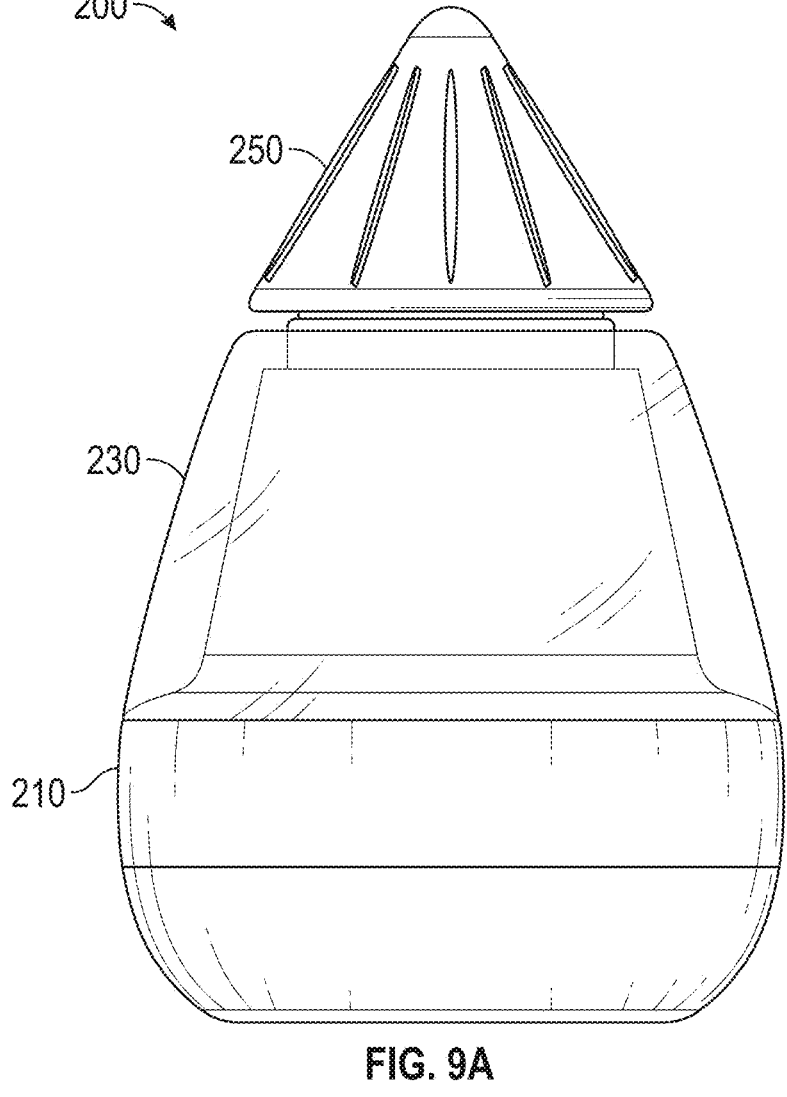
FIG. 9A is an assembled front view of a fourth embodiment of an eye drop dispenser assembly.
Figure 9B:
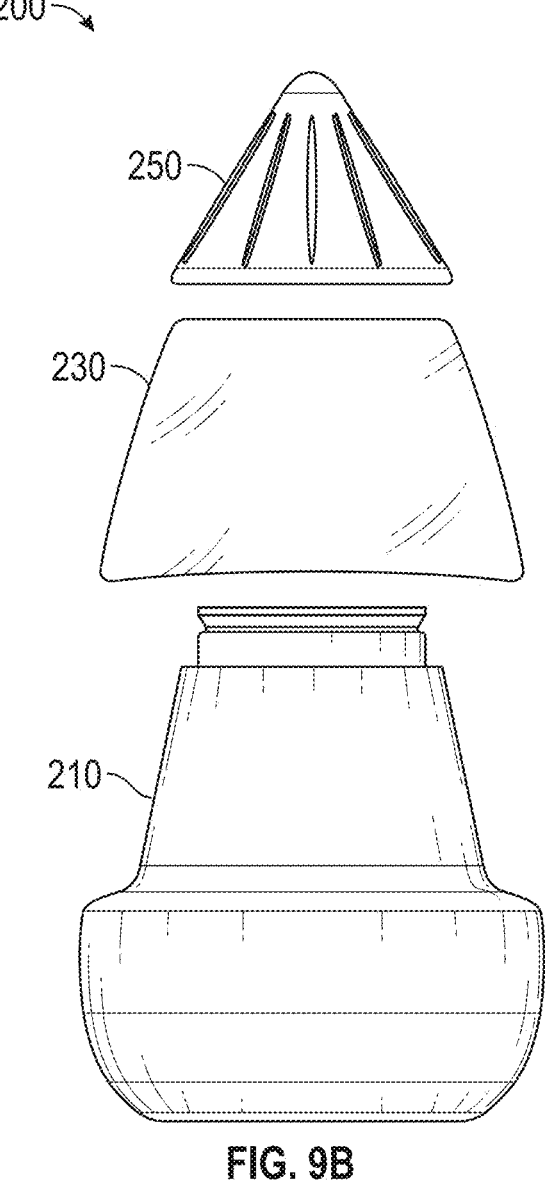
FIG. 9B is an exploded view of the eye drop dispenser assembly of FIG. 9A.

FIGS. 9A-15B illustrate a fourth embodiment of an eye drop dispenser assembly 200 (the "assembly 200"). The assembly 200 includes a detachable and invertible eye cup 230, a dispenser bottle 210, and a cap 250. FIG. 9A shows an assembled front view, of the assembly 200 and FIG. 9B shows and exploded front view of the assembly 200. FIG. 9C shows a front cross section view of the assembly 200 assembled with the eye cup 230 in the stowed position so that the assembly 200 is generally shaped like a water droplet or tear drop. The cap 250 can be a single piece (e.g., monolithic, seamless) with a sidewall 253. The dispenser bottle 210, the eye cup 230 and/or the cap 250 can optionally be made in part or whole of plastic, silicone or rubber. However, the dispenser bottle 210, the eye cup 230 and/or the cap 250 can be made of other suitable materials (e.g., flexible or resilient materials). The cap 250 is removably couplable to the dispenser bottle 210 and can optionally have a conical shape. In one example, the eye cup 230 can be translucent. In one example, the eye cup 230 can be transparent.

Figure 9C:
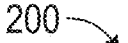
FIG. 9C is a schematic cross-sectional front view of the eye drop dispenser assembly of FIG. 9A.
Figure 9C:
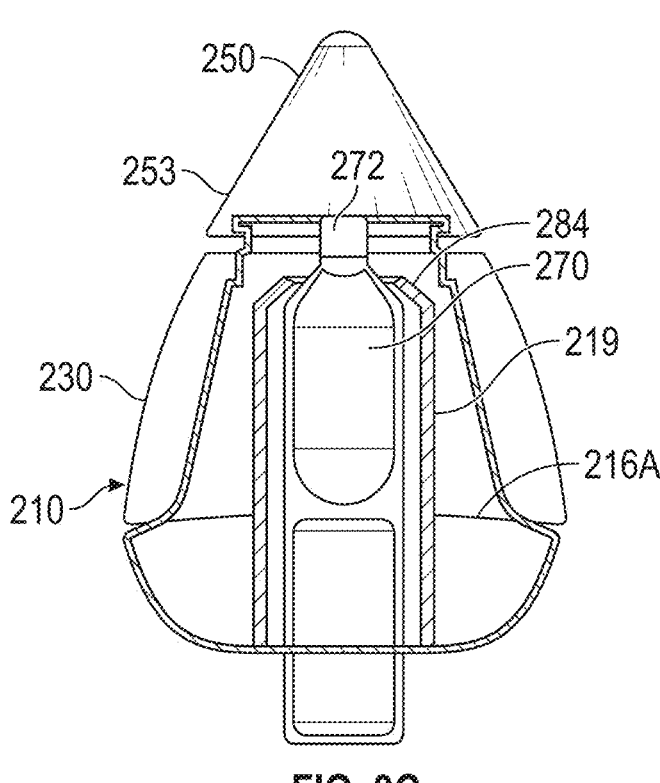
Figure 10:
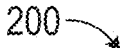
FIG. 10 is a schematic cross-sectional front view of the eye drop dispenser assembly of FIG. 9A with its cap removed and the eye cup in a deployed position extending around a nipple of the dispenser bottle.
Figure 10:
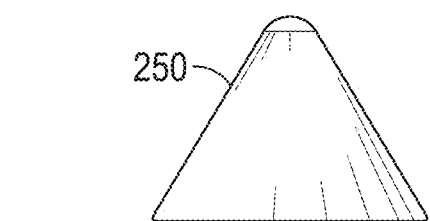
Figure 10:
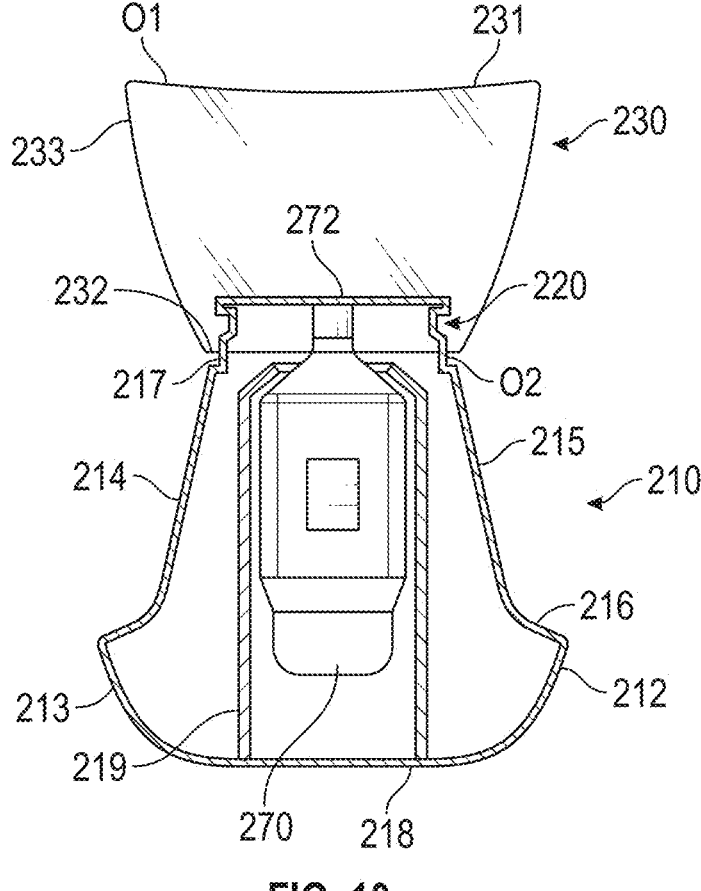
Figure 11:
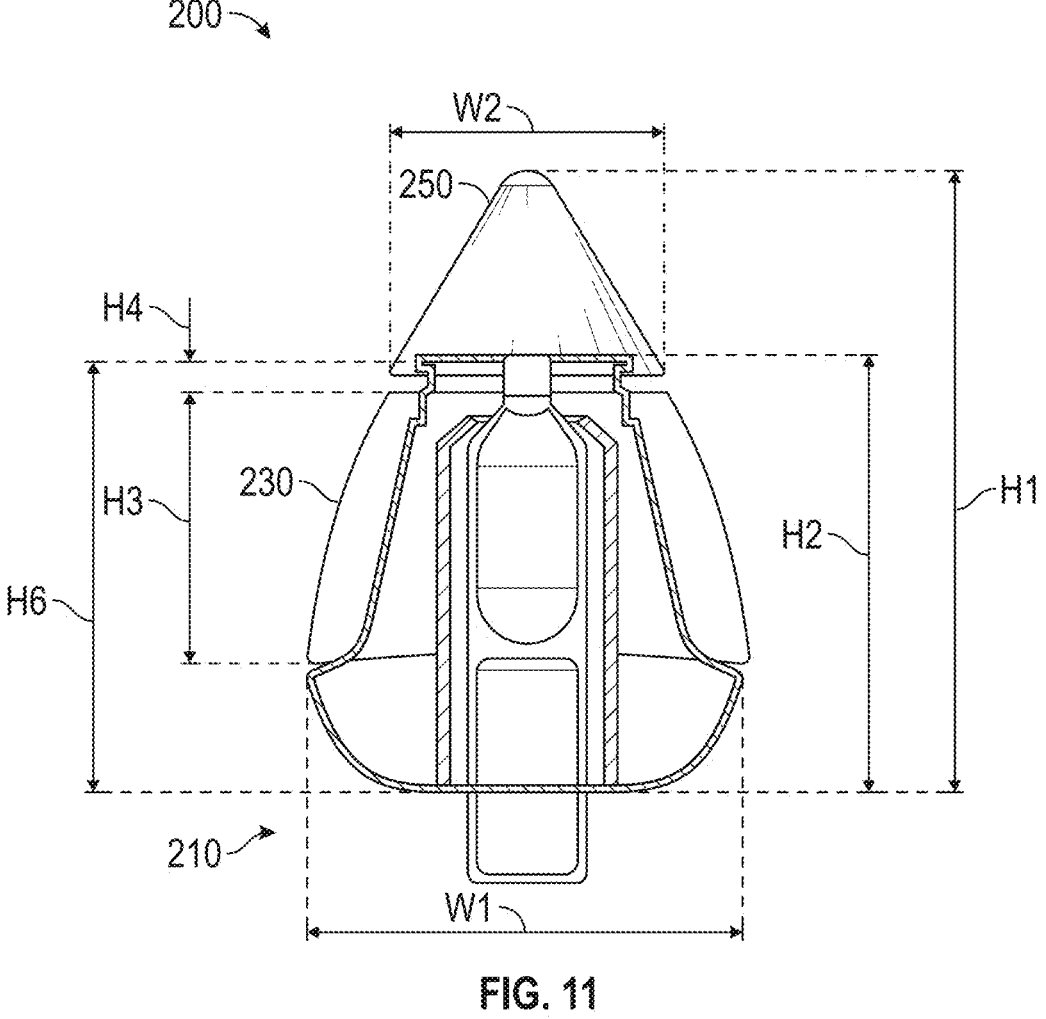
FIG. 11 is another schematic cross-sectional front view of the eye drop dispenser assembly of FIG. 9A.
Figure 12:
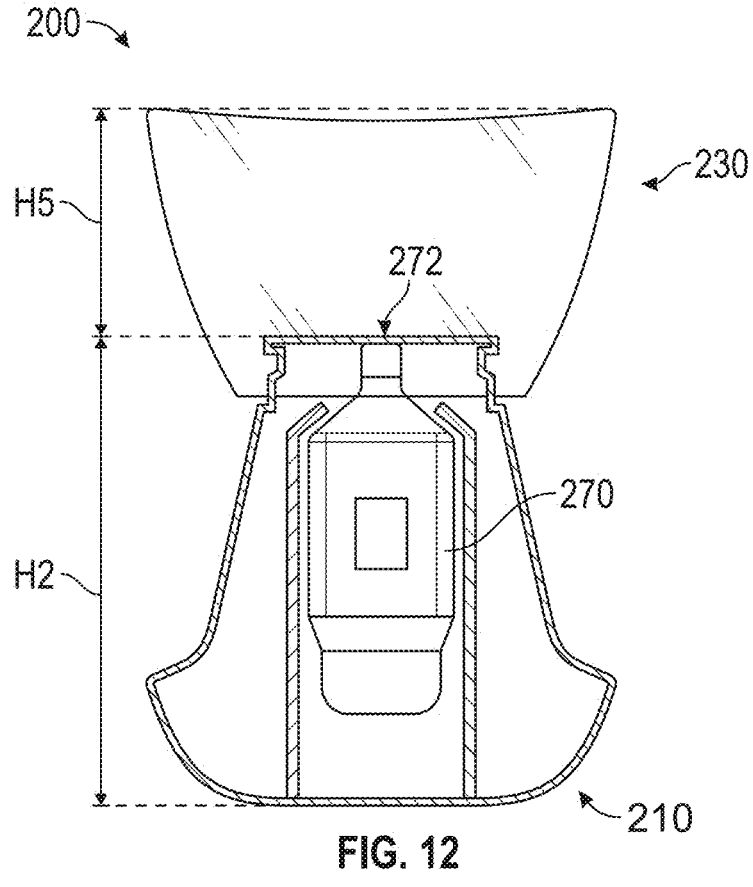
FIG. 12 is another schematic cross-sectional front view of the eye drop dispenser assembly of FIG. 9A with its cap removed and the eye cup in a deployed position extending around a nipple of the dispenser bottle.

As shown in FIG. 10, the dispenser bottle 210 has an internal chamber 219 that can removably receive and hold a single-use vial cartridge 270 (e.g., eye drop cartridge), so the assembly 200 is a single-use vial cartridge eye drop dispenser assembly. FIGS. 9C-13 shows a single-use vial cartridge 270 inserted into the chamber 219, with FIGS. 10 and 12 showing a shorter single-use vial cartridge 270 that entirely resides in the chamber 219 and FIGS. 9C and 11 showing a longer single-use vial cartridge 270 that extends out of the bottom of the dispenser bottle 210. In one example, the eye drops dispensed by the eye drop dispenser assembly 200 can be eye lubricant drops. The liquid can be a formulation for treating a condition of the eyes (e.g., dry eye, bacterial infections, cataracts, glaucoma, or for treating eye injuries). The dispenser bottle 210 can optionally be made of plastic, silicone, rubber, or other suitable resilient or flexible material. The dispenser bottle 210 is a single piece (e.g., a monolithic, seamless single piece). The dispenser bottle 210 can optionally include a lower portion 212 with a sidewall 213 and an upper portion 214 with a sidewall 215, the dispenser bottle 210 having a shoulder 216 (e.g., lower shoulder) between the upper portion 214 and the lower portion 212. In some implementations, the lower portion 212 can be cylindrical. As best shown in FIGS. 9C-10, the shoulder 216 can have a curved or contoured edge 216A on the front, side and rear of the dispenser bottle 210. In one implementation, the sidewall 213 is curved or contoured. In one implementation, the sidewall 215 is generally linear and tapers between the shoulder 216 and a second shoulder 217 (e.g., upper shoulder 217), as shown in FIG. 10. That is, the lower portion 212 has a larger width than the upper portion 214 (e.g., to hold the eye cup).

The dispenser bottle 210 includes a locking mechanism 220 disposed between (e.g., radially between) the second shoulder 217 and the nipple 272. The cap 250 and/or the eye cup 230 can each attach to the dispenser bottle 210 with a locking mechanism 220. In one example, the locking mechanism 220 is a snap-fit. The locking mechanism 220 can additionally or alternatively include one or more threads for threadably coupling with the cap 250 and/or the eye cup 230. Other suitable locking mechanisms can be used. For example, the locking mechanism can be a clip-on mechanism (e.g., that allows the eye cup 230 to clip onto the dispenser bottle 210, such as via multiple clips that clip into depressions in the bottle dispenser), or a press-fit mechanism, where the eye cup 230 is press-fit (e.g., friction fit) onto the dispenser bottle 210. In another example, the locking mechanism 220 can be a threaded coupling, where the eye cup 230 is threadably coupled to threads on the dispenser bottle 210. In another example, the locking mechanism 220 includes one or more recesses (e.g., multiple recesses, two recesses, four recesses) and one or more hooks (e.g., multiple hooks, two hooks, four hooks).

Figure 13:
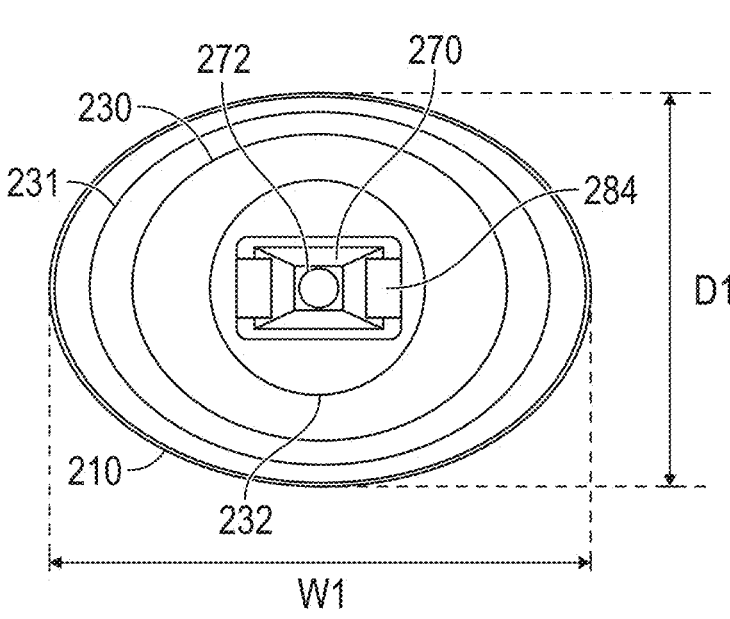
FIG. 13 is a schematic top view of the eye drop dispenser assembly of FIG. 9A with the cap removed.

The eye cup 230, seen in FIG. 10, can have a first edge 231 (e.g., bottom edge), a second edge 232 (e.g., top edge) opposite the first edge 231, and a sidewall 233 that extends between and interconnects the first edge 231 and the second edge 232. The eye cup 230 can optionally be transparent. The eye cup 230 can optionally be made of plastic, silicone, rubber or other suitable resilient or flexible material. The eye cup 230 can be a single piece (e.g., a monolithic, seamless single piece). In other embodiments the eye cup 230 can be multiple pieces that can be assembled together. The eye cup 230 can be hollow with the first edge 231 defining a first opening O1 and the second edge 232 defining a second opening O2 opposite the first opening O1. The eye cup 230 is removably couplable to the dispenser bottle 210. The eye cup 230 can have one or more protrusions or tabs (e.g., multiple, two, four spaced apart protrusions) that extend radially inward from the second edge 232 into the second opening O2. The first opening O1 and first edge 231 can have a larger perimeter than the second opening O2 and second edge 232, the sidewall 233 tapering between the first edge 231 and the second edge 232 (e.g., tapering in a curved manner). As best shown in FIG. 13, the first edge 231 (and first opening O1) can have an oval shape and the second edge 232 (and second opening O2) can have a circular shape. With continued reference to FIG. 10, the first edge 231 can be curved. In one implementation, the first edge 231 is curved or contoured and generally corresponds with a curvature of the contoured edge 216A of the shoulder 216. The second edge 232 can be linear.

With continued reference to FIGS. 9A, 9C, when the eye cup 230 is in the stowed position on the dispenser bottle 210, the eye cup 230 extends around the upper portion 214 (see FIG. 10) of the dispenser bottle 210 (and completely below the nipple 272). In the stowed position (shown e.g. in FIGS. 9A, 9C), the sidewall 233 of the eye cup 230 aligns (e.g., defines a generally continuous edge) with the sidewall 213 of the lower portion 212 of the dispenser bottle 210, and the sidewall 233 also generally aligns with the sidewall 253 of the cap 250, advantageously providing a compact assembly when the eye cup 230 is in the stowed position over the dispenser bottle 210.

With continued reference to FIG. 10, when the eye cup 230 is in the deployed position on the dispenser bottle 210, the eye cup 230 extends around the nipple 272 (and completely above the upper portion 214 of the dispenser bottle 210). In the deployed position, the eye cup 230 is oriented so that the second edge 232 is adjacent the shoulder 217, and coupled to the locking mechanism 220 (as described above), and the first edge 231 and first opening O1 are disposed above the nipple 272 (e.g., so that the first edge 231 defines a topmost end of the assembly 200). In the deployed position, the eye cup 230 can be placed adjacent the eye socket 310 to align the nipple 272 with the eye 300, allowing the user to deliver (e.g., self-administer) solution to the eye 300.

Figure 14:
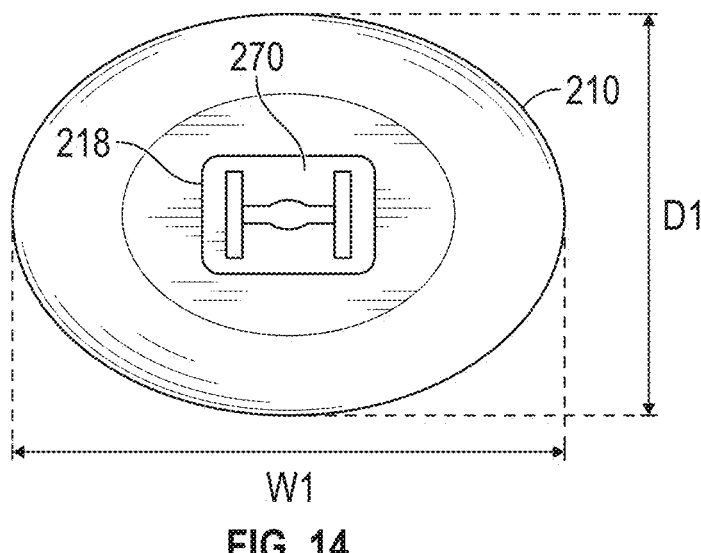
FIG. 14 is a schematic bottom view of the eye drop dispenser assembly of FIG. 9A.

In some embodiments, the single-use vial cartridge 270 can be a single-use vial cartridge. In some embodiments the single-use vial cartridge 270 can be a single-use eye drop vial cartridge. The chamber 219 can include a retention lip 284 which can hold the single-use vial cartridge 270 in place. The dispenser bottle 210 can be squeezed to dispense fluid from the single-use vial cartridge 270. For example, flexing the dispenser bottle 210 can cause the chamber 219 flex and press on the single-use vial cartridge 270, thereby releasing fluid from the single-use vial cartridge 270. The retention lip 284 can be a snap-fit which allows the single-use vial cartridge 270 to be inserted or removed but retains the single-use vial cartridge 270 in its position while in use. In another implementation, the retention lip 284 can be resilient (e.g., act as a spring to allow insertion of the single-use vial cartridge 270 into the chamber 219 and removal of the single-use vial cartridge 270 from the chamber 219). As illustrated in FIG. 14, the bottom surface of the dispenser bottle 210 has an opening 218. The single-use vial cartridge 270 can be inserted into the opening 218. The nipple 272 is integral to the single-use vial cartridge 270. The nipple 272 can extend out past the retention lip 284.

FIGS. 11-14 show schematic views of the eye drop dispenser assembly 200. FIG. 11 shows a front view of the eye drop dispenser assembly 200 with the eye cup 230 in the stowed position. FIG. 12 shows a front view of the eye drop dispenser assembly 200 with the eye cup 230 in the deployed position. FIG. 13 shows a top view of the eye drop dispenser assembly 200 with the eye cup 230 in the deployed position and with the cap 250 removed. FIG. 14 shows a bottom view of the eye drop dispenser assembly 200.

As illustrated in FIG. 11, the assembly 200 has a height H1 between a base of the dispenser bottle 210 and a top of the cap 250, and a height H2 between the base of the dispenser bottle 210 and the end of the nipple 272. The assembly 200 has a height H6 between a top edge of the dispenser bottle 210 and the base of the dispenser bottle 210. In one implementation the height H2 and the height H6 are the same height. In another implementation the height H2 is taller than the height H6. In one implementation, the height H1 is between about 2.5 and 3.5 inches, such as 3 inches, and the height H2 is between about 2.3 and about 3.4 inches, such as 2.9 inches. In one implementation, the height H6 is between about 2.3 and about 3.4 inches, such as 2.9 inches. The eye cup 230 has a height H3 of between about 0.75 inches and about 1.3 inches, such as 1 inch. As illustrated in FIG. 13 the dispenser bottle 210 has a width W1 of between about 1.3 inches and 2.3 inches, such as 1.8 inches, and a depth D1 of between about 1 inch and about 1.5 inches, such as 1.25 inches. The cap 250 can have a width W2 of between about 0.75 inches and about 1.25 inches, such as about 1 inch, and a height H5 of between about 0.75 inches and about 1.25 inches, such as about 1 inch. A gap H4 between the second edge 232 of the eye cup 230 and the bottom of the cap 250 can be between about 0.005 inches and about 0.07 inches, such as about 0.05 inches. When in the deployed or inverted position, the eye cup 230 can extend a height H5 past the nipple 272. In one example, illustrated in FIG. 12, the height H5 is between about 0.1 inches and about 0.6 inches, such as about 0.25 inch and facilitates a soft landing of the eye drop onto the eye. The height H5 can also help ensure the eye drop is delivered into the eye and does not run off the eye (e.g., onto the user's face, such as cheek).

Figure 15A:
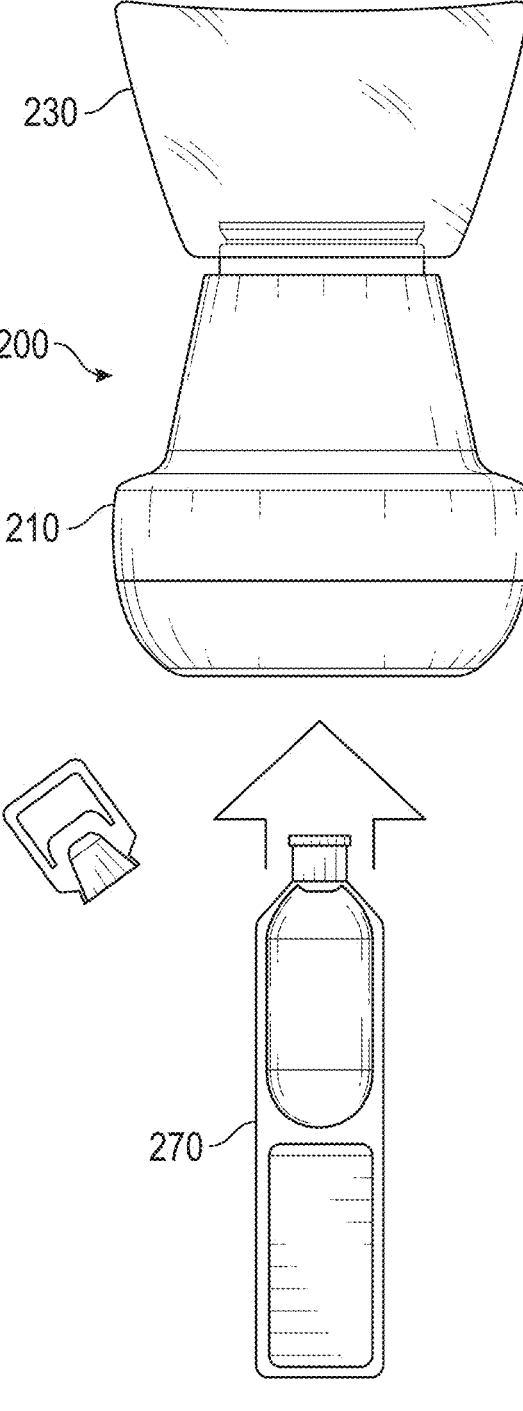
FIG. 15A is a schematic view of the eye drop dispenser of FIG. 9A illustrating the insertion of the single-use vial cartridge into the eye drop dispenser bottle.
Figure 15B:
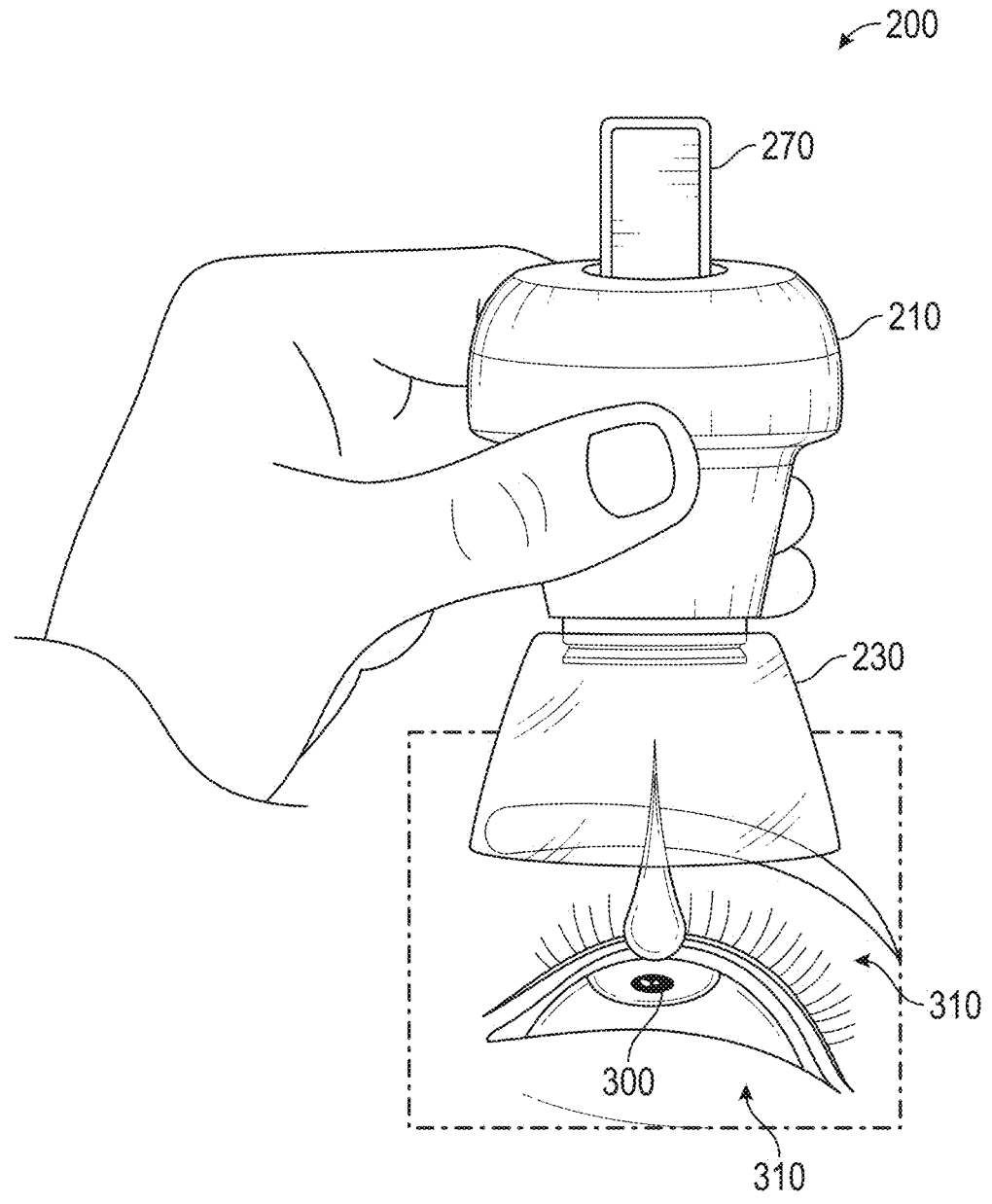
FIG. 15B is a schematic view of the eye drop dispenser of FIG. 9A in an inverted position over a user's eye to deliver an eye drop thereto.

FIG. 15A illustrates the insertion of a single-use vial cartridge 270 into the assembly 200. FIG. 15B illustrates the eye drop dispenser 200 in an inverted position over an eye 300 to deliver an eye drop thereto. As shown in FIG. 15B, the assembly 200 can be inverted and disposed over an eye 300 so that the eye cup 230 is disposed over (e.g., in contact with) an eye socket 310 of the eye 300 (e.g., to that the eye cup 230 provides a supporting structure that supports the dispenser bottle 210 in an inverted position on the eye socket 310 of the user's eye 300). The user can then squeeze the dispenser bottle 210 to dispense one or more drops into the eye 300. This arrangement advantageously facilitates self-administration of a solution to a user's eye 300. The user simply removes the cap 250 from the dispenser bottle 210, attaches the eye cup 230 to the dispenser bottle 210, removes the top or tab of the single-use vial cartridge 270, inserts the single-use vial cartridge 270 into the dispenser bottle 210 (e.g., as shown FIG. 15A), inverts the dispenser bottle 210, places the eye cup 230 against the eye socket 310 of the eye 300, and squeezes the dispenser bottle 210 to dispense the solution.

The assembly 200 is advantageously compact because of the removable eye cup 230. Additionally, the assembly 200 is advantageously easy to use (e.g., it is easy to remove the cap 250, remove the eye cup 230 from the stored position and reattach the cap 250 in the deployed (inverted) position, remove the top or tab of a single-use vial cartridge 270, insert the single-use vial cartridge 270, position the eye cup 230 over the eye 300, and dispense the eye solution (e.g., eye drops, eye wash, eye lid wash) in the optimal location without contaminating the nipple 272 or touching the nipple 272 to the eye 300. This facilitates safe, user-friendly, self-administration of eye solution to a user's eye 300. The assembly 200 advantageously facilitates self-administration of the eye solution by a user without needing assistance from someone else.

Figure 16A:
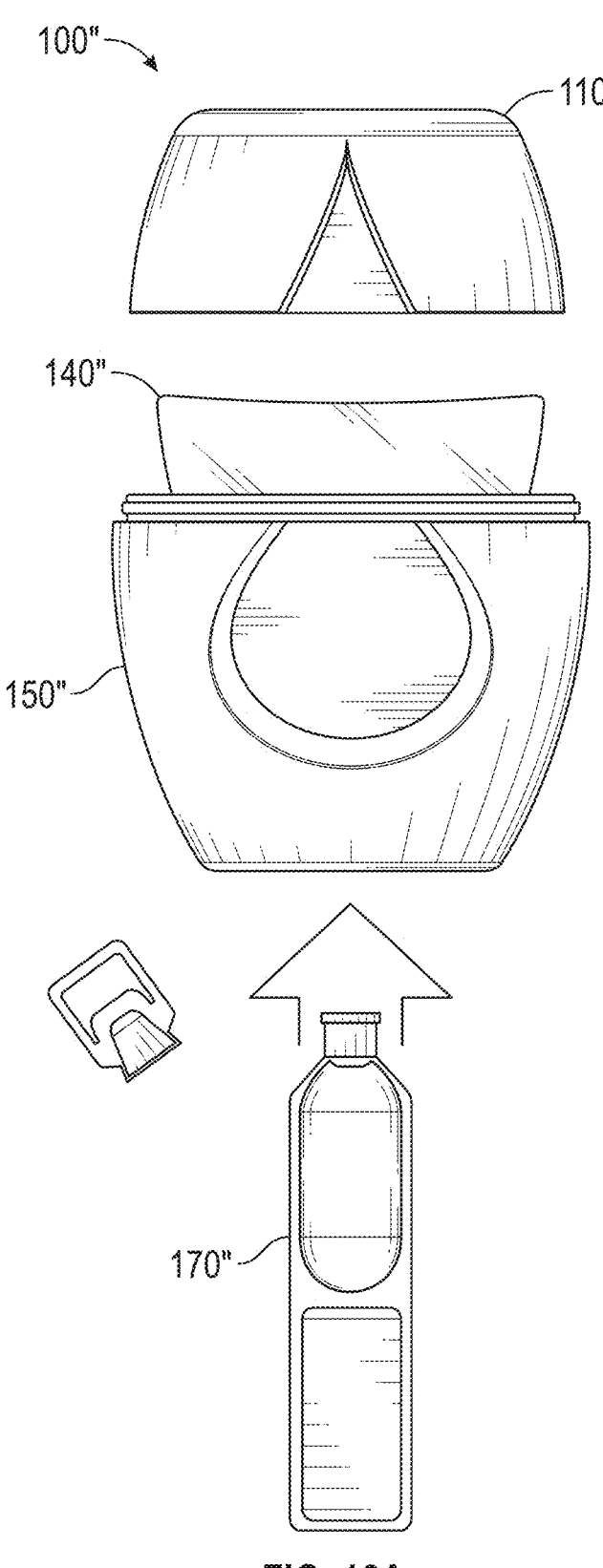
FIG. 16A is a schematic view of the eye drop dispenser of FIG. 7A illustrating the insertion of the single-use vial cartridge into the eye drop dispenser bottle.
Figure 16B:
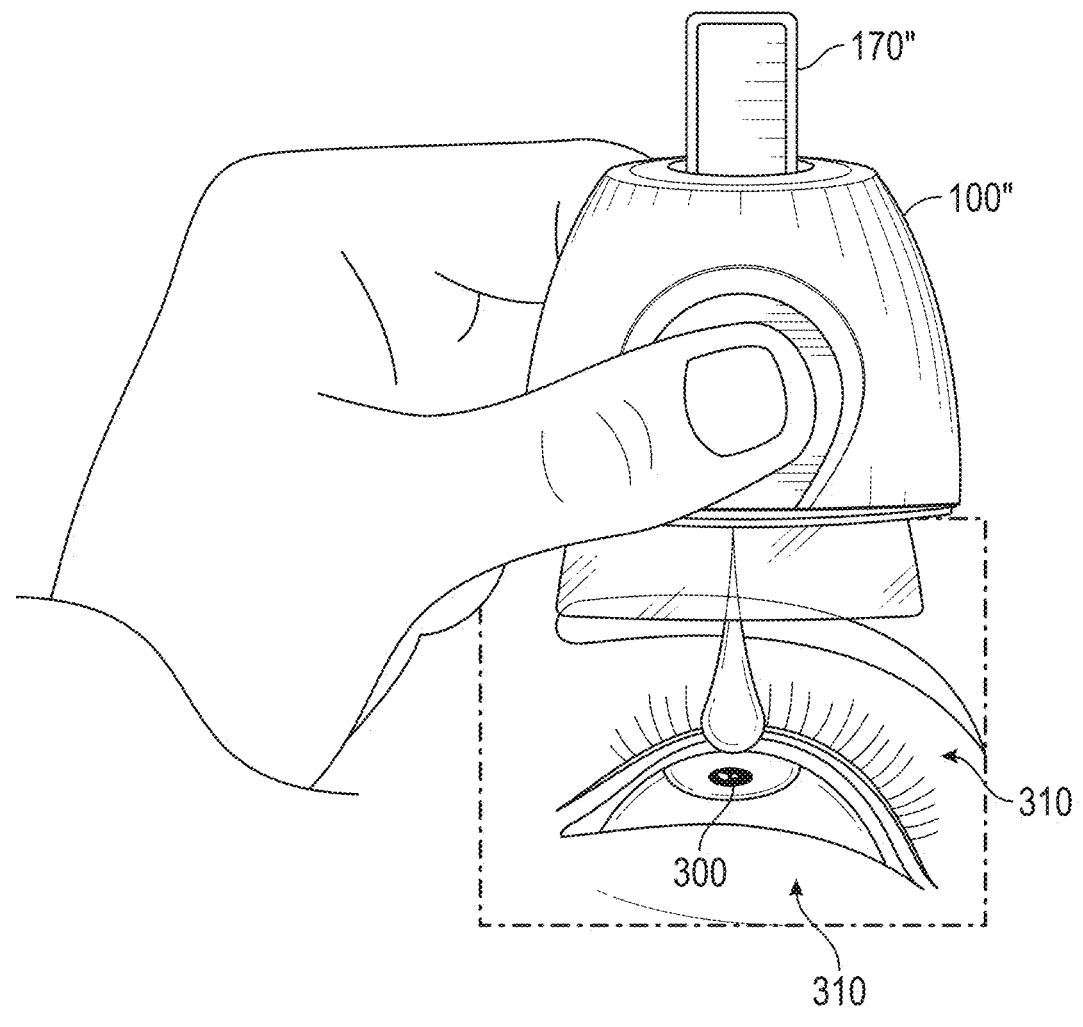
FIG. 16B is a schematic view of the eye drop dispenser of FIG. 7A in an inverted position over a user's eye to deliver an eye drop thereto.
Figure 16C:
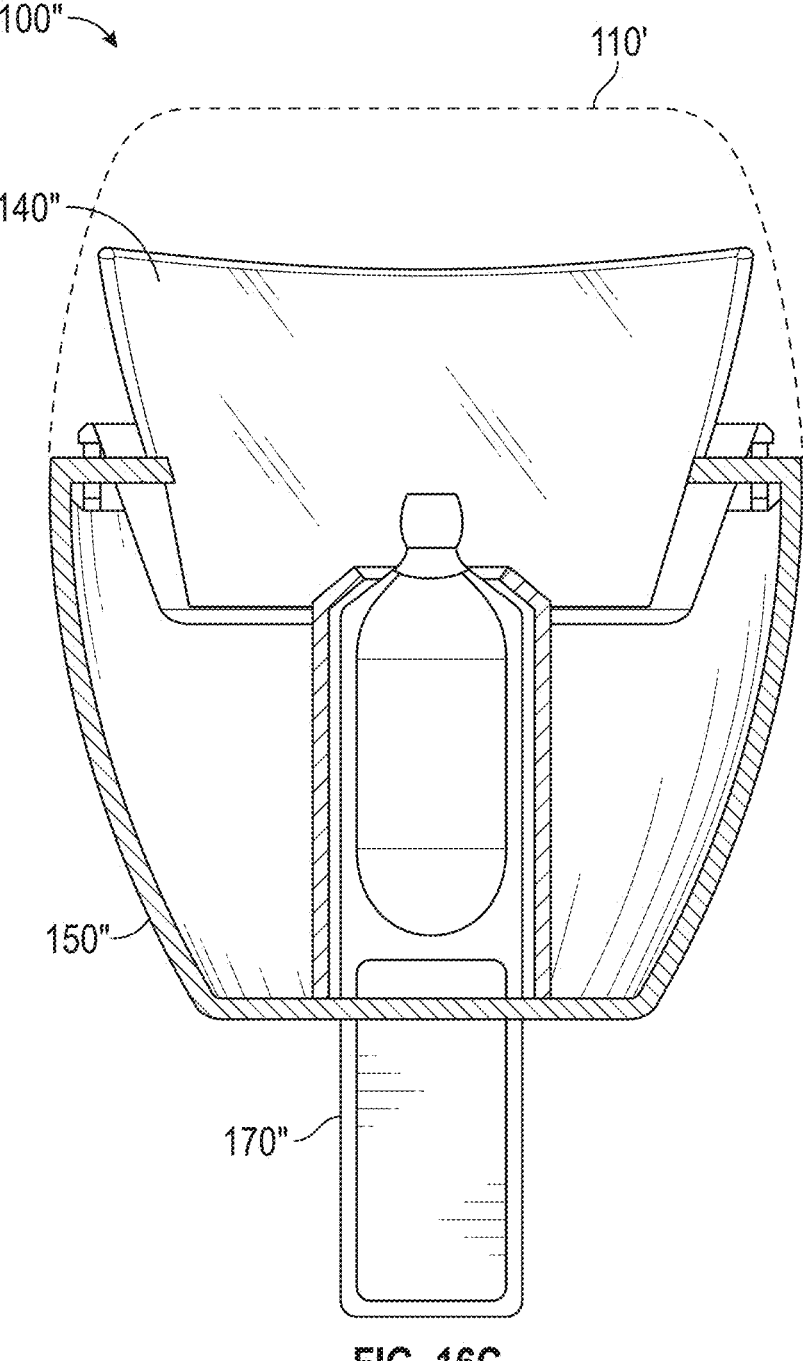
FIG. 16C is a schematic cross-sectional view of the eye drop dispenser in FIG. 16A.

FIG. 16A illustrates the insertion of a single-use vial cartridge 170" into the assembly 100". FIG. 16B illustrates the dispenser assembly 100" in an inverted position over an eye 300 to deliver an eye drop thereto. FIG. 16C shows a cross-sectional view of the assembly 100" in FIG. 16A with the single-use vial cartridge 170" (removably) inserted therein. As shown in FIG. 16B, the assembly 100" can be inverted and disposed over an eye 300 so that the eye cup 140" is disposed over (e.g., in contact with) an eye socket 310 of the eye 300 (e.g., to that the eye cup 140" provides a supporting structure that supports the dispenser bottle 150" in an inverted position on the eye socket 310 of the user's eye 300). The user can then squeeze the dispenser bottle 150" to dispense the eye solution (e.g., one or more drops) into or over the eye 300. This arrangement advantageously facilitates self-administration of a solution to a user's eye 300 and is user friendly as it does not require the user to assemble the eye cup onto the bottle and can apply it with one hand. Rather, the user simply removes the cap 110" from the dispenser bottle 150", removes the top or tab of the single-use vial cartridge 170", inserts the single-use vial cartridge 170" into the dispenser bottle 150" (e.g., as shown FIG. 16A), inverts the dispenser bottle 150", places the eye cup 140" against the eye socket 310 of the eye 300, and squeezes the dispenser bottle 150" to dispense the solution.

Figure 17:
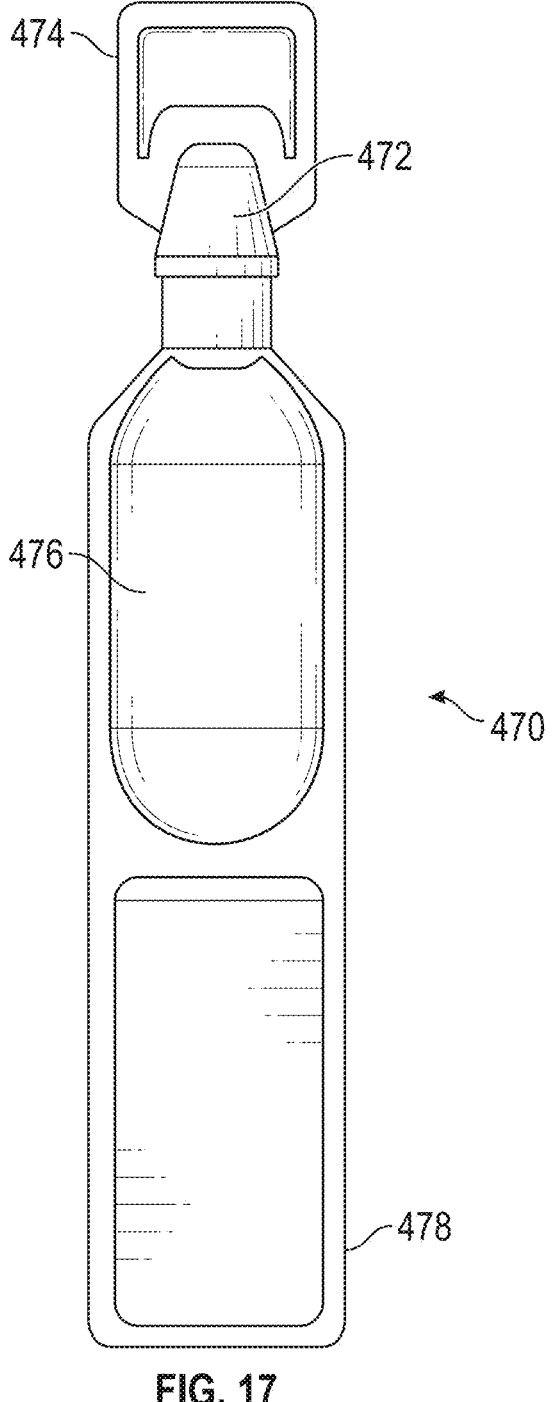
FIG. 17 is a schematic front view of a single-use vial cartridge.

FIG. 17 illustrates a single-use vial cartridge 470. Each feature of the single-use vial cartridge 470 applies to the single-use vial cartridges 170" and 270 described herein. The single-use vial cartridge 470 includes a nipple 472 and a cover tab 474. The nipple 472 is fluidically attached to a fluid reservoir 476. Below the fluid reservoir 476 is an insertion tab 478. The insertion tab 478 can be used to position the single-use vial cartridge 470 within a dispenser bottle. The insertion tab 478 can also be used to remove the single-use vial cartridge 470 from the dispenser bottle. The cover tab 474 can be removed to dispense fluid (e.g., eye drops, eye wash, eye lid cleaner and/or wash) from the fluid reservoir 476 through the nipple 472. The single-use vial cartridge 470 can optionally be made in part or whole of plastic (e.g., polypropylene).

Figure 18A:
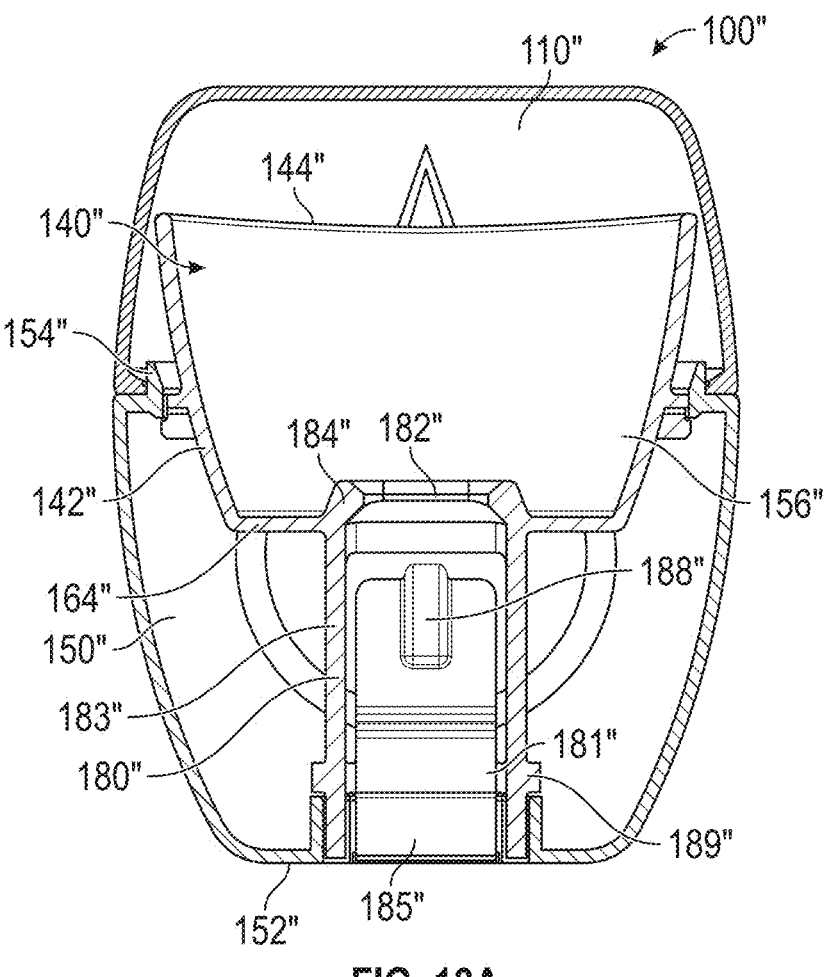
FIG. 18A is a schematic front cross-sectional view of a dispenser assembly.
Figure 18B:
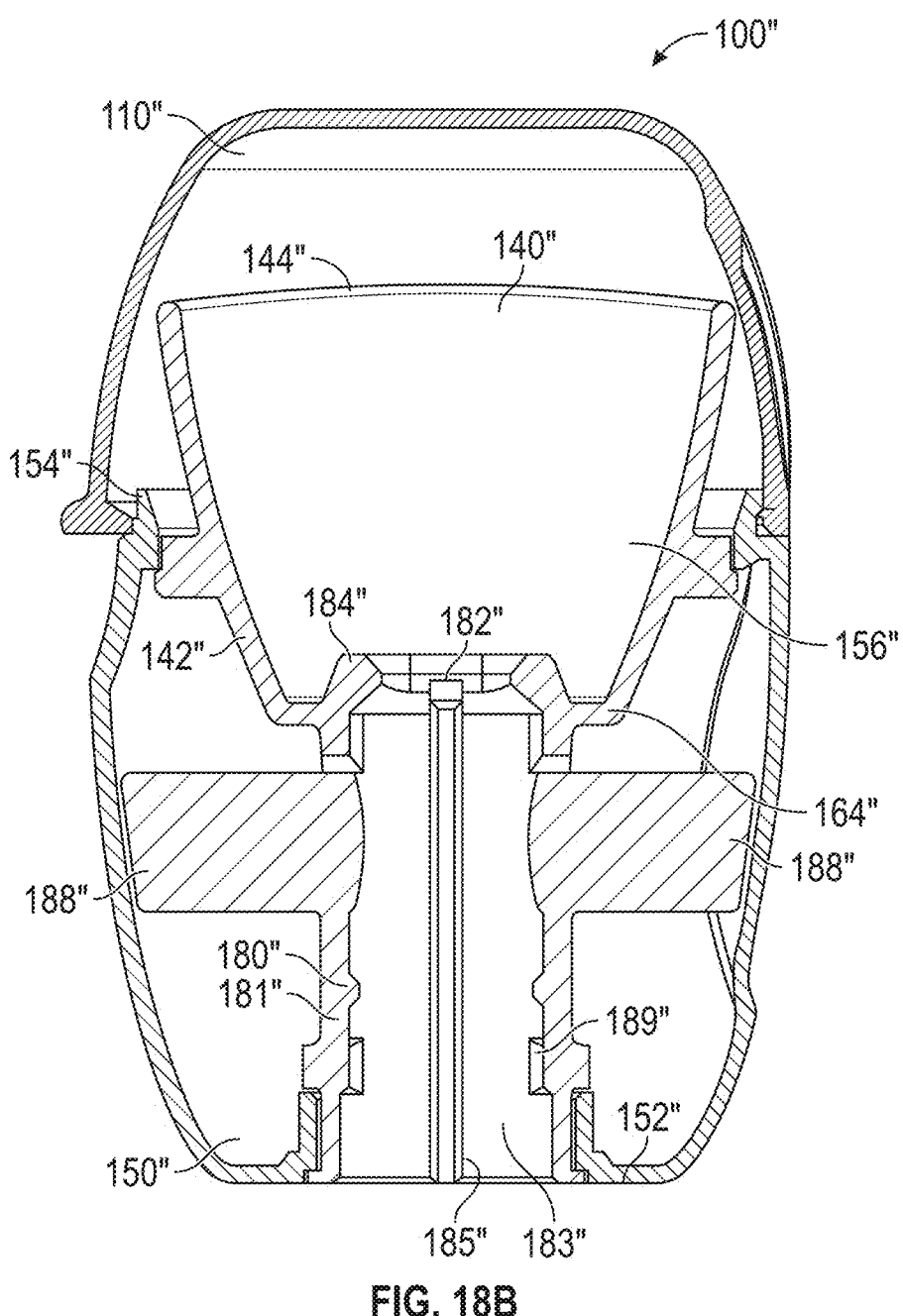
FIG. 18B is a schematic side cross-sectional view of the dispenser assembly in FIG. 18A.

FIG. 18A illustrates a schematic front cross-sectional view of a dispenser assembly 100". FIG. 18B illustrates a schematic side cross-sectional view of a dispenser assembly 100" (e.g., a view offset 90 degrees from the view in FIG. 18A). Some of the features of the assembly 100" are similar to features described with reference to FIGS. 7A and 8A. Therefore, the structure and description for the various features of the assembly 100″ and how it is operated and controlled in FIGS. 7A and 8A are understood to also apply to the corresponding features of the assembly 100″ illustrated in FIGS. 18A and 18B, and vice versa, except as described below. The dispenser assembly 100″ can removably or releasably house a cartridge vial (not shown) to deliver a solution (e.g., eye drops, eye wash, eye lid cleaner and/or wash) onto or over the eye or a portion thereof (e.g., eye lid).

The dispenser assembly 100″ includes a dispenser bottle 150″ (e.g., dispenser body) with a base 152″. Additionally, the cap 110″ described above can attach to the dispenser bottle 150″ in substantially the same way the cap 110′ attaches to the dispenser bottle 150′. The cap 110″ can be removably couplable to an end of the dispenser bottle 150″ opposite to (e.g., distal from) the base 152″. In some embodiments, the base 152″ is flat. In other embodiments, a portion, but less than all, of the base 152″ is flat.

The cross-section illustrated in FIG. 18A is taken at a midpoint of the depth G″ of the assembly 100″ (see FIG. 8A). The dispenser bottle 150″ has a chamber 180″ (cartridge chamber) that can releasably and removably hold a single-use vial cartridge 170″ (not pictured). The single-use vial cartridge 170″ is (removably) inserted into the chamber 180″ from the bottom of the dispenser bottle 150″ (e.g., the end of the dispenser bottle 150″ opposite the eye cup 140″) via an opening 185″ and it is held in the chamber 180″ by a retention element 189″. The retention element 189″ is a circumferential ridge which extends into the chamber 180″ to create a friction fit between the retention element 189″ and the vial cartridge 170″. In some embodiments, the retention element 189″ can be an annular snap-fit. The chamber 180″ has an opening 182″ defined within the surface 164″. The opening 182″ can include a retention lip 184″ which can aid in holding the single-use vial cartridge 170″ in place, providing an axial limit for the body of the vial cartridge 170″. The retention lip 184″ can be a snap-fit which allows the single-use vial cartridge 170″ to be inserted or removed but retains the single-use vial cartridge 170″ in its position while in use. In another implementation, the retention lip 184″ can be resilient (e.g., act as a spring to allow insertion of the single-use vial cartridge 170″ into the chamber 180″ and removal of the single-use vial cartridge 170″ from the chamber 180″), such as a resilient tapered wall. The retention lip 184″ can in one example extend circumferentially about a central axis of the dispenser bottle 150″. In another example, the retention lip 184″ can be two angled or tapered walls on opposite sides of the central axis of the dispenser bottle 150″. The dispenser bottle 150″ can be squeezed to dispense fluid from the single-use vial cartridge 170″. As illustrated, the chamber 180″ is defined by a frame that extends from the opening 185″ to the opening 182″ and includes side wall portions 183″ positioned along two sides of the chamber 180″. A pair of arms 188″ can extend outward from the chamber 180″ towards the walls of the dispenser bottle 150″ so that the arms 188″ are integral to the chamber 180″ and are positioned between the chamber 180″ and the dispenser bottle 150″. The arms 188″ are positioned along two sides of the chamber 180″ between the side wall portions 183″ so that the chamber 180″ has a rectangular cross section. The arms 188″ can be attached to living hinges 181″ (e.g., resilient walls) which connect to the frame of the chamber 180″ proximal to the opening 185″. As illustrated in FIG. 18B, a first arm 188″ can extend towards the front wall of the dispenser bottle 150″ and a second arm 188″ can extend towards the rear wall of the dispenser bottle 150″. In some embodiments, the arms 188″ can extend toward the side walls of the dispenser bottle 150″. The arms 188″ can pivot on the living hinges 181″ into the chamber 180″ and towards the central axis of the dispenser bottle 150″ (e.g., the arms 188″ can move relative to the frame of the chamber 180″). The arms 188″ can transfer a force or pressure applied to the dispenser bottle 150″ by a user when squeezing the dispenser bottle 150″ to the single-use vial cartridge 170″. For example, flexing the dispenser bottle 150″ can push on the arms 188″, causing the chamber 180″ to press on the single-use vial cartridge 170″ and compress the single-use vial cartridge 170″, thereby releasing fluid from the single-use vial cartridge 170″ via the nipple of the single-use vial cartridge 170″.

In some embodiments, the chamber 180″, arms 188″, and eye cup 140″ are integral and together form a single body (e.g., the chamber 180″, arms 188″, and eye cup 140″ form a single seamless body or are molded simultaneously). In some embodiments, the chamber 180″ and arms 188″ are integral and together form a single body. In some embodiments, the eye cup 140″ can attach to the dispenser bottle 150″ via a snap-fit connection or a threaded attachment. In some embodiments, the chamber 180″ can attach to the dispenser bottle 150″ via a snap-fit connection or a threaded attachment. In some embodiments, the eye cup 140″ can attach to the chamber 180″. The eye cup 140″ can attach to the chamber 180″ via a snap-fit connection or a threaded attachment.

Figure 19A:
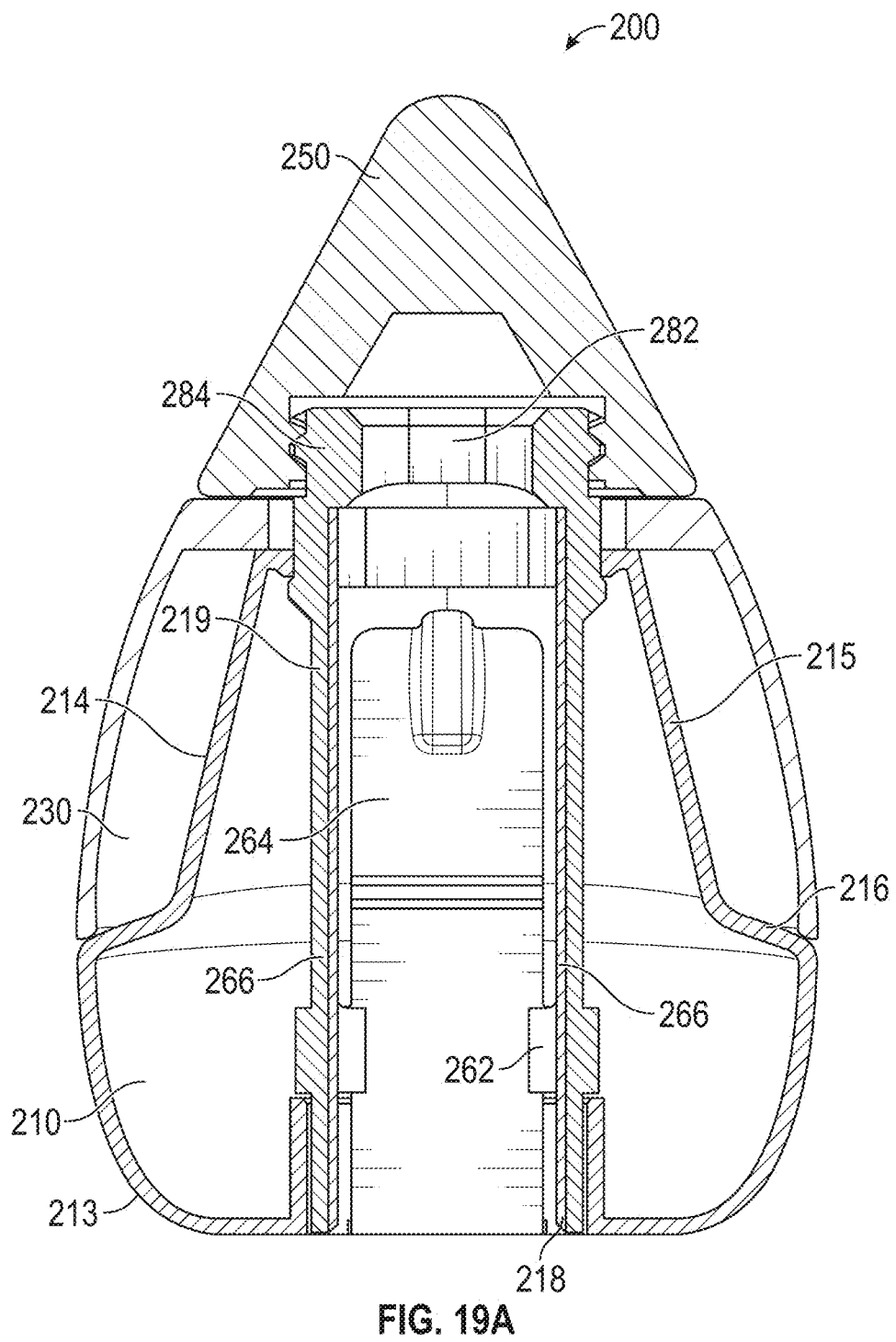
FIG. 19A is a schematic front cross-sectional view of a dispenser assembly.
Figure 19B:
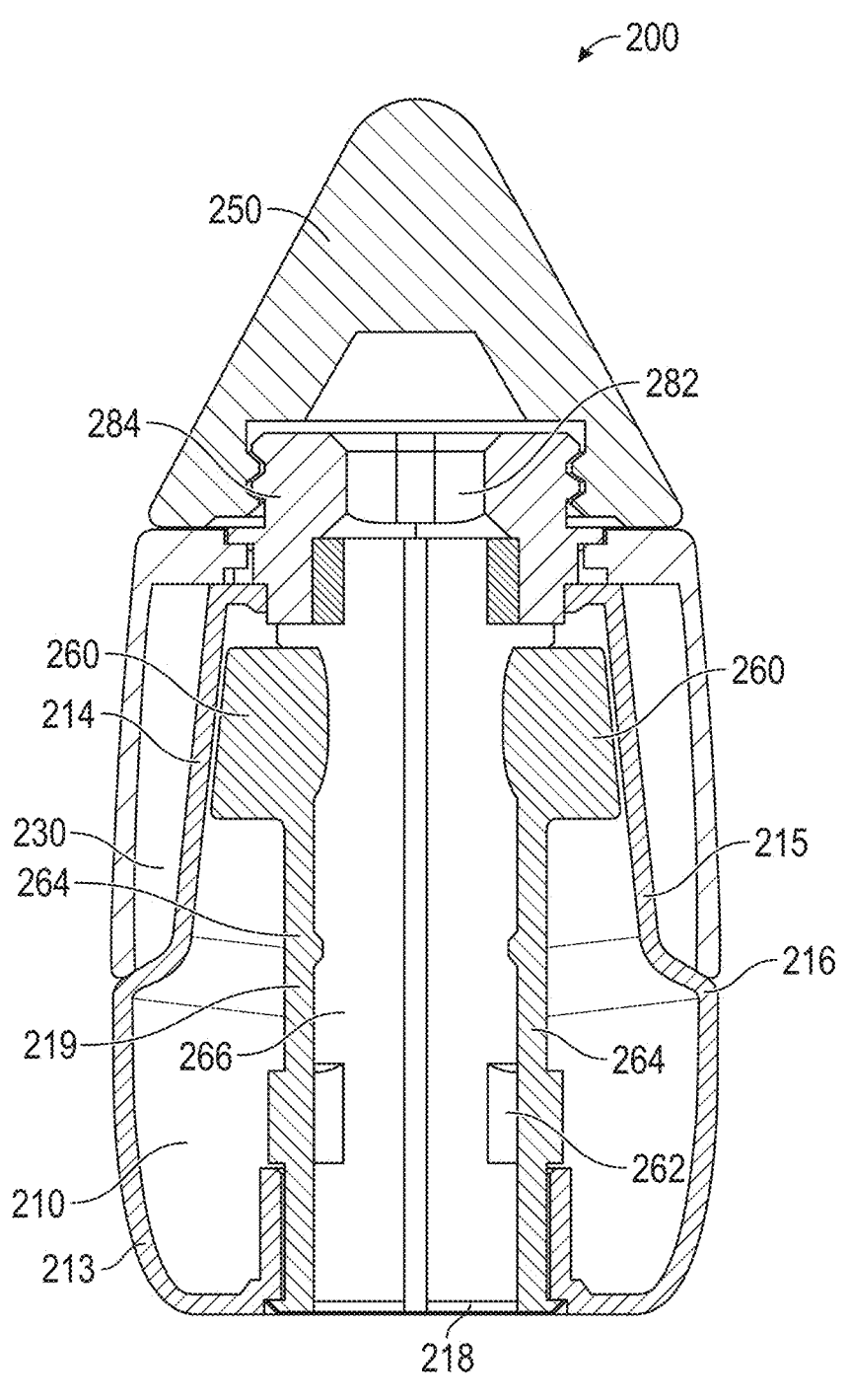
FIG. 19B is a schematic side cross-sectional view of the dispenser assembly in FIG. 19A.

FIG. 19A illustrates a schematic front cross-sectional view of a dispenser assembly 200. FIG. 19B illustrates a schematic side cross-sectional view of a dispenser assembly 200 (e.g., a view offset 90 degrees from the view in FIG. 18A). Some of the features of the assembly 200 are similar to features described with reference to FIGS. 9A-12. Therefore, the structure and description for the various features of the assembly 200 and how it is operated and controlled in FIGS. 9A-12 are understood to also apply to the corresponding features of the assembly 200 illustrated in FIGS. 19A and 19B, and vice versa, except as described below. The dispenser assembly 200 can removably or releasably house a cartridge vial (not shown) to deliver a solution (e.g., eye drops, eye wash, eye lid cleaner and/or wash) onto or over the eye or a portion thereof (e.g., eye lid).

The dispenser bottle 210 has a chamber 219 that can hold a single-use vial cartridge 270 (not pictured). The single-use vial cartridge 270 can be (removably) inserted into the chamber 219 from an opening 218 in the bottom of the dispenser bottle 210 (e.g., the end of the dispenser bottle 210 opposite the eye cup 230) and it is held in the chamber 219 by a retention element 262. The retention element 262 is a circumferential ridge which extends into the chamber 219 to create a friction fit between the retention element 262 and the vial cartridge 270. In some embodiments, the retention element 262 can be an annular snap-fit. The chamber 219 has an opening 282 at the top of the dispenser bottle 210 (e.g., the end of the dispenser bottle 210 where the eye cup 230 attaches to the dispenser bottle 210). The opening 282 can include a retention lip 284 which can hold the single-use vial cartridge 270 in place. The retention lip 284 can be a snap-fit which allows the single-use vial cartridge 270 to be inserted or removed but retains the single-use vial cartridge 270 in its position while in use. In another implementation, the retention lip 284 can be resilient (e.g., act as a spring to allow insertion of the single-use vial cartridge 270 into the chamber 219 and removal of the single-use vial cartridge 270 from the chamber 219). The dispenser bottle 210 can be squeezed to dispense fluid from the single-use vial cartridge 270. As illustrated, the chamber 219 is defined by a frame that extends from the opening 218 to the opening 282 and includes side wall portions 266 positioned at along two sides of the chamber 219. A pair of arms 260 can extend outward from the chamber 219 towards the walls of the dispenser bottle 210 so that the arms 260 are positioned between the chamber 219 and the dispenser bottle 210. The arms 260 are positioned along two sides of the chamber 219 between the side wall portions 266. The arms 260 can be attached to living hinges 264 (e.g., resilient walls) which connect to the frame of the chamber 219 proximal to the opening 218. As illustrated, a first arm 260 can extend towards the front wall of the dispenser bottle 210 and a second arm 260 can extend towards the rear wall of the dispenser bottle 210. In some embodiments, the arms 260 can extend towards the side walls of the dispenser bottle 210. The arms 260 can pivot on the living hinges 264 into the chamber 219 and towards the central axis of the dispenser bottle 210 (e.g., the arms 260 can move relative to the frame of the chamber 219). The arms 260 can transfer a force or pressure applied to the dispenser bottle 210 to the single-use vial cartridge 270. For example, flexing the dispenser bottle 210 can push on the arms 260 causing the chamber 219 to compress and press on the single-use vial cartridge 270, thereby releasing fluid from via the nipple of the single-use vial cartridge 270.

In some embodiments, the chamber 219 and arms 260 are integral and together form a single body seamless body. In some embodiments, the chamber 219 can attach to the dispenser bottle 210 via a snap-fit connection or a threaded attachment. In some embodiments, the eye cup 230 can attach to the chamber 219. The eye cup 230 can attach to the chamber 219 via a snap-fit connection or a threaded attachment. In some embodiments, the cap 250 can attach to the chamber 219 near the retention lip 284 via a snap-fit connection or a threaded attachment.

While certain embodiments of the inventions have been described, these embodiments have been presented by way of example only and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A dispenser assembly, comprising:
a dispenser bottle comprising:
a circumferential sidewall;
a first surface; and
a chamber extending from an opening in a second surface to an opening at a base of the dispenser bottle, the chamber having a chamber wall spaced inward from the circumferential sidewall to define a gap between the chamber wall and the circumferential sidewall, the chamber configured to removably receive and hold a vial therein; and
an eye cup coupled to the second surface of the dispenser bottle and extending distally from the second surface, the eye cup comprising:
a circumferential sidewall disposed around the opening of the chamber; and
a distal edge configured to be disposed over an eye socket to facilitate delivery of a solution from the vial into a user's eye.

2. The dispenser assembly of claim 1, wherein the first surface and the second surface each form an external surface of the dispenser bottle.

3. The dispenser assembly of claim 1, wherein the second surface is disposed in a recessed cavity of the dispenser bottle.

4. The dispenser assembly of claim 1, wherein the second surface is proximal of the first surface.

5. The dispenser assembly of claim 1, further comprising a retention lip extending from the chamber, the retention lip configured to retain the vial in the chamber.

6. The dispenser assembly of claim 5, wherein the retention lip extends distally of the second surface.

7. The dispenser assembly of claim 6, wherein the retention lip comprises a resilient material.

8. The dispenser assembly of claim 1, wherein the circumferential sidewall of the dispenser bottle is configured to flex and press on a single-use vial disposed in the chamber.

9. The dispenser assembly of claim 1, wherein the chamber is integral to the dispenser bottle.

10. The dispenser assembly of claim 1, wherein the circumferential sidewall tapers outward from the second surface to the distal edge.

11. The dispenser assembly of claim 1, further comprising a cap removably couplable to the dispenser bottle over the chamber.

12. A dispenser assembly, comprising:
a dispenser bottle having:
a coupling mechanism; and
a chamber having a chamber wall extending from an opening in a surface proximate to the coupling mechanism and to an opening at a bottom surface of the dispenser bottle, the chamber wall spaced inward from a circumferential sidewall to define a gap between the chamber wall and the circumferential sidewall; and
an eye cup having a first open end and a second open end opposite the first open end and configured to removably fit over at least a portion of the dispenser bottle, the eye cup being couplable to the coupling mechanism of the dispenser bottle in a stowed position where the eye cup is disposed about an upper portion of the dispenser bottle, the eye cup further being couplable to the coupling mechanism of the dispenser bottle in a deployed position where the eye cup is disposed so that it extends around and distally from the coupling mechanism.

13. The dispenser assembly of claim 12, wherein the chamber is configured to hold a vial.

14. The dispenser assembly of claim 12, wherein the surface proximate to the coupling mechanism is proximal of the coupling mechanism.

15. The dispenser assembly of claim 12, wherein the chamber is configured to flex and press on a vial disposed in the chamber.

16. The dispenser assembly of claim 12, wherein the upper portion is recessed relative to a lower portion, and wherein an outer surface of the eye cup circumferentially aligns with an outer surface of the lower portion of the dispenser bottle when in the stowed position.

17. The dispenser assembly of claim 12, further comprising a cap configured to couple to the coupling mechanism.

18. The dispenser assembly of claim 17, wherein the cap is configured to couple to the coupling mechanism while the eye cup is in the stowed position.

19. The dispenser assembly of claim 12, wherein the chamber is integral to the dispenser bottle.

20. The dispenser assembly of claim 19, wherein the coupling mechanism is integral to the chamber.

* * * * *